(12) United States Patent
Ritter et al.

(10) Patent No.: US 6,241,671 B1
(45) Date of Patent: Jun. 5, 2001

(54) OPEN FIELD SYSTEM FOR MAGNETIC SURGERY

(75) Inventors: Rogers C. Ritter, Charlottesville, VA (US); Jeffrey M. Garibaldi, St. Louis, MO (US); Charles Wolfersberger, Ferguson, MO (US); Francis M. Creighton; Peter R. Werp, both of St. Louis, MO (US); Bevil J. Hogg, Town & Country, MO (US); Walter M. Blume, Webster Groves, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/211,723

(22) Filed: Dec. 14, 1998

Related U.S. Application Data

(60) Provisional application No. 60/107,144, filed on Nov. 3, 1998.

(51) Int. Cl.[7] .............................. A61B 6/00; H02N 15/00
(52) U.S. Cl. ............................................. 600/427; 361/141
(58) Field of Search .................................... 600/407, 410, 600/434, 424, 427, 409; 128/898, 899; 361/141; 335/177, 207, 216, 296, 297, 298; 324/307, 309, 318, 319

(56) References Cited

U.S. PATENT DOCUMENTS

| | | | | |
|---|---|---|---|---|
| 3,674,014 | * | 7/1972 | Tillander ............................... | 128/2.05 |
| 4,694,868 | * | 9/1987 | Jahnke et al. ......................... | 140/92.1 |
| 4,774,468 | * | 9/1988 | Bydder ................................. | 324/318 |
| 4,869,247 | * | 9/1989 | Howard, III ........................ | 128/303.1 |
| 4,951,674 | * | 8/1990 | Zanakis et al. ...................... | 324/653 |
| 5,125,888 | * | 6/1992 | Howard et al. ...................... | 600/12 |
| 5,442,289 | * | 8/1995 | Dilorio et al. ........................ | 324/248 |
| 5,654,864 | * | 8/1997 | Ritter et al. ........................... | 361/141 |
| 5,667,469 | * | 9/1997 | Zhang et al. ........................... | 600/9 |
| 5,747,996 | * | 5/1998 | Fuchs ............................... | 324/207.17 |
| 5,752,514 | * | 5/1998 | Okamura et al. ................... | 128/653.1 |
| 5,779,694 | * | 7/1998 | Howard et al. ..................... | 604/891.1 |
| 5,845,646 | * | 12/1998 | Lemelson ............................. | 128/899 |
| 5,936,580 | * | 8/1999 | Van Puijenbrock ................. | 343/700 |
| 6,014,580 | * | 1/2000 | Blume et al. ........................ | 600/424 |
| 6,015,377 | * | 1/2000 | Brown et al. ........................... | 600/9 |
| 6,128,174 | * | 10/2000 | Ritter et al. .......................... | 361/143 |
| 6,144,872 | * | 11/2000 | Graetz ................................. | 600/409 |
| 6,157,853 | * | 12/2000 | Blume et al. ........................ | 600/426 |

OTHER PUBLICATIONS

"A New Magnet System for 'Intravascular Navigation'," Shyam B. Yodh, et al, Med and Biol. Engrg. vol. 6 pp. 143–147 (1968).

(List continued on next page.)

*Primary Examiner*—Marvin M. Lateef
*Assistant Examiner*—Elenimantis Mercader
(74) *Attorney, Agent, or Firm*—HarnessDickey & Pierce

(57) ABSTRACT

A system of navigating a magnetic medical device within that part of a patient located within an operating region of the system, the system comprising magnets, and preferably electromagnets, arranged to provide a magnetic field sufficient to navigate the magnetic medical device within the operating region. There are preferably three magnetic coils arranged in mutually perpendicular planes such that their axes intersect in the operating region. The magnetic coils are sized and arranged so that a patient can easily access the operating region to allow virtually any portion of the patient to be positioned within the operating region. The openness of the magnetic system allows access to the operating region by a bi-planer imaging system.

90 Claims, 27 Drawing Sheets

OTHER PUBLICATIONS

"Magnetically Controlled Intravascular Catheter," John Alksne, Surgery, vol. 61, No. 1, 339–345 (1968).

"The "Pod", a New Magnetic Device for Medical Applications," E.H. Frei, et al, in Proceedings of 16$^{th}$ Ann. Conference on Engineering in Medicine and Biology, vol. 5, Nov. 18–20, 1963, pp. 156–157.

"Magnetic Propulsion of Diagnostic or Therapeutic Elements Through the Body Ducts of Animal or Human Patients," U.S. Patent 3,358,676 Dec. 19, 1967, E.H. Frei et al.

"Selective Angiography with a Catheter Guided by a Magnet," H. Tillander, IEEE Transactions on Magnetics, vol. Mag–6, No. 2, 355–358 (1970).

"Cerebral Arteriovenous Malformations Treated with Magnetically Guided Emboli," Jack Driller et al, in Proc. Of 25$^{th}$ Ann Conf on Engineering and Biology, vol. 14 (12972), p. 306.

* cited by examiner

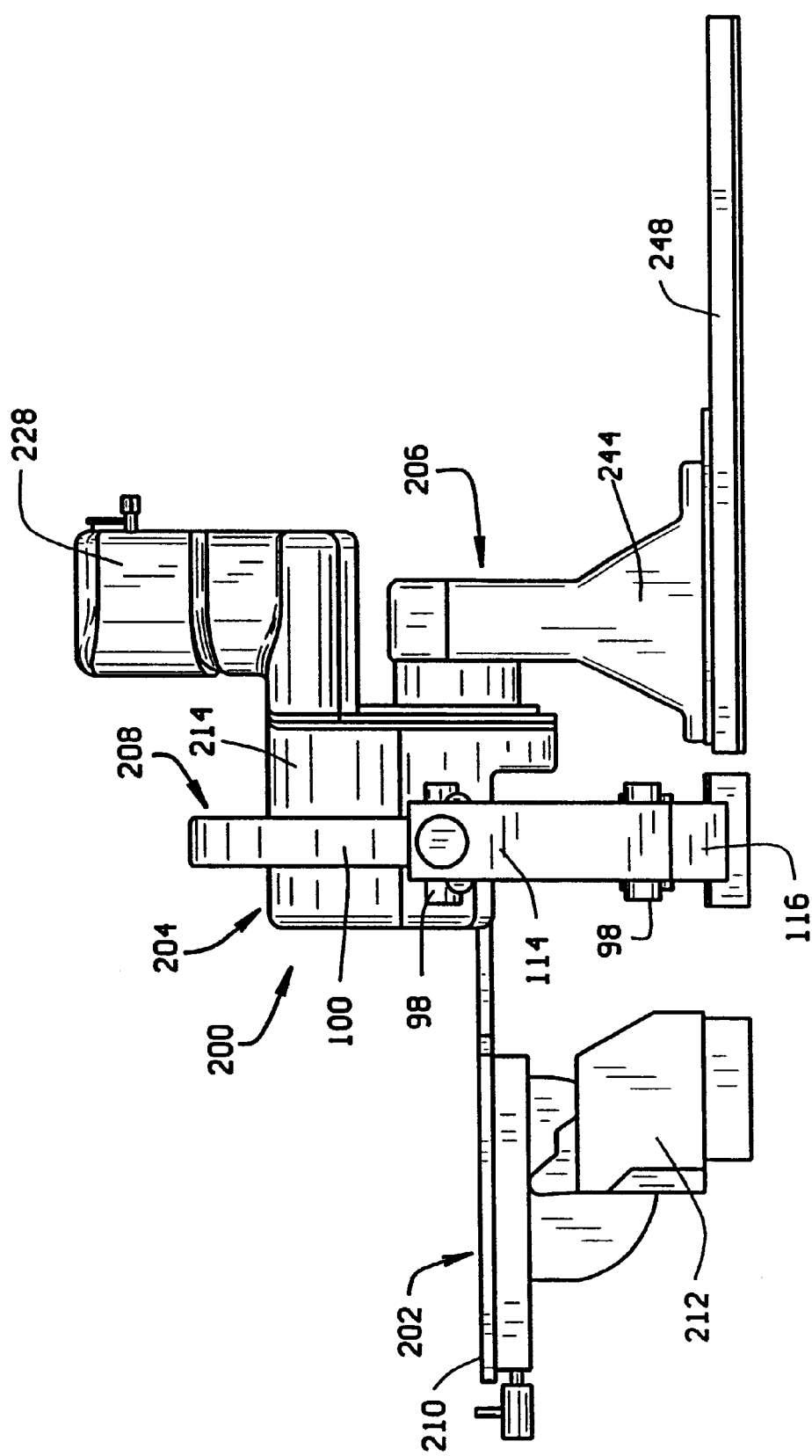

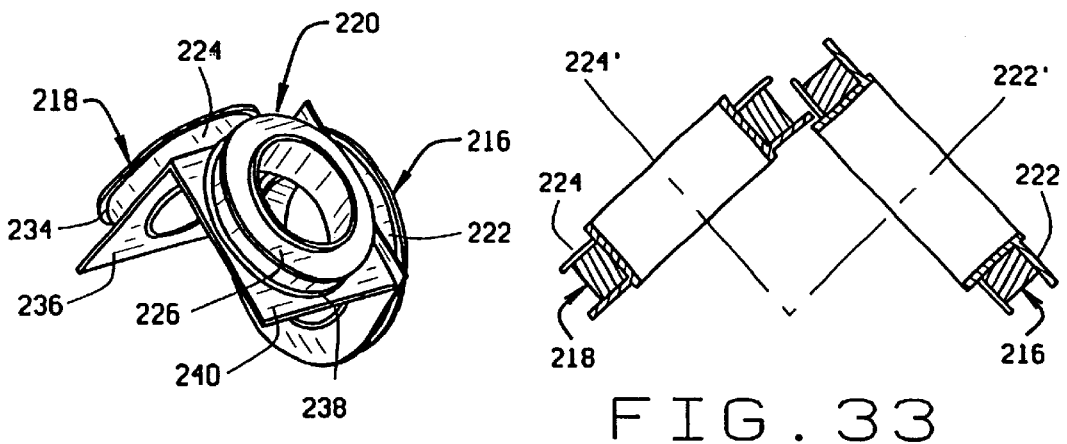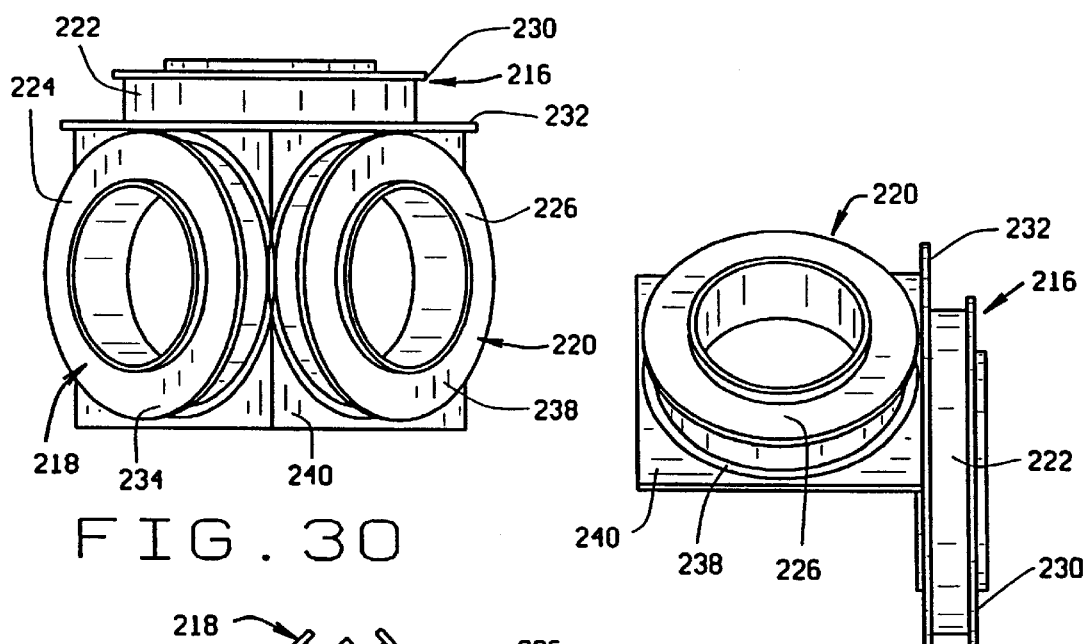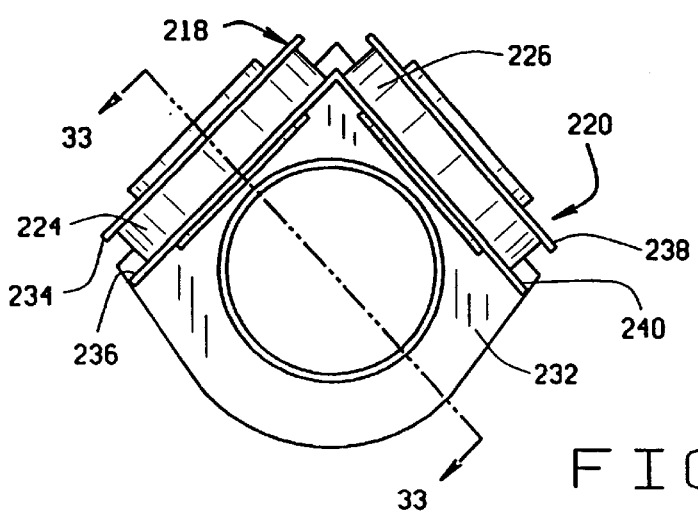

OPEN FIELD SYSTEM FOR MAGNETIC SURGERY

CROSS-REFERENCE TO RELATED APPLICATION

This Application claims priority of Provisional Patent Application Serial No. 60/107,144 filed Nov. 3, 1998, incorporated herein by reference.

FIELD OF THE INVENTION

This invention relates to a magnetic surgery system, and in particular to an open magnetic surgery system that provides greater access to the patient for imaging and other purposes.

BACKGROUND OF THE INVENTION

A wide variety of minimally invasive surgical procedures have been developed which employ catheters, endoscopes, or other similar devices that can be navigated remotely from their distal ends. The catheter, endoscope or other medical device is manipulated through the tissue or through an existing body lumen or cavity using a guide wire or other mechanical means. Examples of such procedures include the treatment of aneurysms, arterial ventricular malformations, atrial fibrillation, ureteral stones, and investigations of lumen such as sigmoidoscopies and colonoscopies, ERCP's; and biliary duct examinations. While these procedures are highly beneficial to the patient, they are difficult and time consuming for the physician. Some procedures can only be performed by the most skilled surgeons.

Several attempts have been made to use magnets to assist in such surgeries, as documented in "A New Magnet System for 'Intravascular Navigation'," Shyam B. Yodh et al., Med. And Biol. Engrg., Vol. 6, pp. 143–147 (1968); "Magnetically Controlled Intravascular Catheter," John Alksne, Surgery, Vol. 61, no. 1, 339–345 (1968); "The 'Pod', a New Magnetic Device for Medical Applications," E. H. Frei et al., in Proceedings of 16th Ann. Conference on Engineering in Medicine and Biology, Vol. 5, Nov. 18–20, 1963, pp. 156–157; "Magnetic Propulsion of Diagnostic or Therapeutic Elements Through the Body Ducts of Animal or Human Patients," U.S. Pat. No. 3,358,676, issued Dec. 19, 1967 to E. H. Frei et al.; "Selective Angiography with a Catheter Guided by a Magnet," H. Tillander, IEEE Transactions on Magnetics, Vol. Mag-6, No. 2, 355–375 (1970); and "Cerebral Arteriovenous Malformations Treated with Magnetically Guided Emboli," Jack Driller et al., in Proc. of 25th Ann. Conf. On Engineering and Biology, Vol. 14 (1972), p. 306.

For various reasons these previous attempts at magnetically assisted surgery have not proven to be successful, nor are they widely used. One reason has been the inability of the previous systems to adequately guide the probes within the vessels, partly for mechanical and hydrodynamic reasons, partly from the lack of adequate computer and control technology, and partly because of an inability to provide adequate real time imaging for the procedures. Because of the small size of the vessels to be navigated, extremely high resolution and flexibly moveable fluoroscopes are needed to provide adequate imaging. These fluoroscopes are large instruments. Even now, accessibility of adequate imaging in the presence of the large magnets needed to move small magnetic guiding "seeds" on medical devices is difficult.

Systems have been disclosed for magnetic guidance of catheters and guidewires to facilitate navigation of difficult vascular turns. An example of such a system is provided in U.S. utility patent application Ser. No. 09/020,934, filed Feb. 9, 1998, entitled "Method and Apparatus Using Shaped Field of Repositionable Magnet to Guide Implant," incorporated by reference herein in its entirety. Other effective magnetic surgical systems have required relatively large magnets. Often, superconducting magnets with associated cooling systems are used to generate the most effective magnetic fields, and two magnets for each spatial direction have been provided for a total of six magnets, each having an associated cooling system. Such a system is disclosed in U.S. patent application Ser. No. 08/920,446, filed Aug. 29, 1997, entitled "Method and Apparatus for Magnetically Controlling Motion Direction of a Mechanically Pushed Catheter," incorporated by reference herein in its entirety.

Imaging means can be used in conjunction with magnetically guided surgery. An example of such a system is described in U.S. utility patent application Ser. No. 09/020,798, filed Feb. 9, 1998, entitled "Device and Method for Specifying Magnetic Field for Surgical Applications," incorporated by reference herein in its entirety. While magnetically guided surgery with such systems is practical, the sheer bulk and size of their magnetic systems results in less accessibility of the operating region of the patient than a surgeon might prefer. Also, imaging equipment (such as X-ray equipment) for observing the operating region has been fixed to the magnetic system assembly, or otherwise been immobile or of limited mobility relative to the magnets and/or the patient. This relative immobility tends to reduce the ability of the surgeons to see the medical operating device in the patient, making the operation somewhat more difficult for the surgeon and somewhat riskier for the patient than might otherwise be the case. Another difficulty with using magnetic systems for these purposes is that the conventional fluoroscopes cannot be used in magnetic fields of any significant magnitude. It would therefore be desirable to provide an apparatus for magnetically-assisted surgery that provides flexibility of both the imaging and of the magnetic field application.

A difficulty associated with magnetic guidance is that relatively large magnetic fields are needed to guide the small magnets that can fit within the small vessels and body lumens. The large superconducting coils employed in previous systems to provide these relatively large magnetic fields put huge amounts of energy into the fields. Because of the tendency for the coils to quench if ramped (powered) up or down too rapidly, the rate at which current can be applied or removed from the coils is limited, even with advantageous ramping methods such as the "constant power ramp." See U.S. patent application Ser. No. 08/921,298, filed Aug. 29, 1997, entitled "Method and Apparatus for Rapidly Changing a Magnetic Field Produced by Electromagnets," incorporated by reference herein in its entirety. The distance between the coil and the operating region is also a factor in ramping time, and thus it is desirable to provide a system having coils located and sized so as to optimize both the "openness" described above in terms of the accessibility to the surgeon of an operating region of a patient, and the rapidity of field directional changes.

Unless otherwise noted, all referenced issued patents, patent applications, and other documents are hereby incorporated by reference in their entirety.

SUMMARY OF THE INVENTION

The present invention provides an open system for navigating a magnetic medical device within that part of a patient located within an operating region of the system. Generally, the system comprises a plurality of magnets configured and arranged to provide a magnetic field effective within the operating region to navigate the magnetic medical device within the operating region, while providing access to the patent for imaging and other purpose.

The magnets are preferably electromagnetic coils, and more preferably superconducting electromagnetic coils. The magnets are preferably capable of generating a magnetic field of at least about 0.1 Tesla in an operating region of at least about two inches by two inches by two inches, and more preferably in an operating region of at least about five inches by five inches by five inches. In a preferred embodiment, the magnets can generate a field of about 0.3 Tesla in any direction within the operating region. The operating region is preferably at least about twelve inches from each of the magnets, such that the system can accommodate a sphere having a radius of about twelve inches to provide sufficient room for a patient and imaging apparatus.

Generally, a single magnet is arranged and configured to provide a magnetic field along at least one of a plurality of oblique axes extending through the operating region, and one or more magnets are arranged and configured to provide a magnetic field along each of the other of said oblique axes, said magnetic fields being effective to controllably navigate the magnetic medical device within substantially the entirety of the operating region. Preferably there are three magnets in three mutually perpendicular planes, arranged such that their axes converge in the operating region, and more preferably they are arranged so that their axes intersect in the operating region. The magnets are arranged in an open configuration, i.e., the patient typically does not have to extend through a magnet coil to reach the operating region, as was required in previous magnetic surgery systems. The coils are sized and positioned so that their respective near field lines are substantially straight within the operating region.

The coils are preferably fixed relative to each other, but may be moveable relative to the patient. The magnets are preferably enclosed within a concave housing sufficiently large to accommodate the patient and imaging devices, yet small enough to fit within the conventional supports for imaging devices. In the most preferred embodiment, the shell has a generally hemispherical shape, with an inner diameter of at least about twenty-four inches and an outer diameter of no more than about fifty inches. The generally hemispherical shell is mounted so that its axis is at an angle between vertical and horizontal and thus faces generally downwardly, but so that the shell can be rotated about a generally vertical axis.

To increase the flexibility of the system, there is preferably an opening in the housing, aligned with one of the coils, through which a portion of the patient's body can extend to bring another portion of the patient's body into the system's operating region. The system can include a patient support for supporting and for moving the patient relative to the operating region of the system.

The system further comprises an imaging system for providing images of the operating region. The imaging system comprises at least one, and preferably two imaging devices. Each imaging device comprises an imaging plate and an x-ray imaging source. The imaging plates are preferably ones that are minimally affected by magnetic fields, such as amorphous silicon imaging plates. The imaging devices are preferably fixedly mounted with respect to each other, in mutually perpendicular directions to provide perpendicular bi-planar imaging of the operating region.

The imaging devices are mounted on a movable support, independently of the magnet coils. The support allows the imaging devices to be moved about three axes, and may be, for example a conventional C-arm support. This allows the imaging devices to be moved relative to the operating region, to provide the surgeon the most advantageous view of the procedure. The three axes of movement of the imaging devices preferably intersect, and more preferably they intersect in the operating region, and most preferably they intersect at the same point where the axes of the magnets coils intersect. This provides the greatest flexibility of imaging in the operating region.

More specifically, the system of this invention provides for navigating a magnetic medical device within that portion of a patient within an operating region of the system. The system includes a support for at least a portion of the patient. The system also includes a magnet assembly including electromagnetic coils arranged and configured so that the axes of the coils converge, and a magnet mount holding the magnet assembly so that the center of the operating region (i.e., the convergence of the axes) is within the desired portion of the patient on the patient support. An imaging assembly for providing an image of the operating region comprises at least one imaging plate and an imaging beam source mounted on an imaging support to be on opposite sides of the operating region, and a mechanism for selectively pivoting the support about three mutually perpendicular axes.

In the preferred embodiment, a total of three super conducting magnets coils are configured so that each of their central axes lies generally along an axis of an orthogonal coordinate system having its origin approximately centered within the operating region. The magnets are supported by a generally hemispherical housing and each magnet is of sufficient strength to provide a magnetic field in the direction of its respective central axis having a generally consistent strength of about 0.3 Tesla throughout substantially the entirety of the operating region. A control adjusts the strength of the magnetic field of each of said magnet coils to thereby controllably navigate the magnetic medical device within that part of a patient within the operating region.

The method of navigating according to this invention includes applying a magnetic field to the magnetic medical device in the operating region with at least three electromagnetic coils contained within a magnet housing to navigate the medical device within the operating region; and providing an image of the magnetic medical device in the operating region with an imaging apparatus comprising at least one imaging plate and an imaging beam source, the imaging plate and imaging beam source being on opposite sides of the operating region, with the imaging plate being positioned between the operating region and the magnet housing. The imaging plate and imaging beam source are movable about three mutually perpendicular axes which extend through the operating region. These axes preferably extend through the point of intersection of the axes of the magnets.

The present invention also includes a method of determining a distribution of ramping times for the electromagnetic coils in the system. This method includes calculating for a selected magnetic field magnitude and direction, the currents needed in each coil to provide the selected magnetic field magnitude and direction at a point in an operating region; estimating, for each of the calculated currents, a ramping time required to reach the calculated current; and repeating the current calculating step and the ramping time estimating step for a plurality of different points in the operating region, and for selected magnetic field magnitudes and directions to obtain a distribution of ramping times as a function of selected magnetic field magnitude and direction for the system.

The present invention also includes a method of optimizing the design of the system, comprising selecting a maximum ramping time not to be exceeded by a selected percentage of navigational direction changes of the magnetic medical device; determining a distribution of ramping times; determining a percentage of ramping times in the distribution of ramping times that the selected maximum ramping time is exceeded; and modifying at least one property of at least one of the electromagnetic coils, the at least one property including at least one property selected from the group consisting of coil radius, coil cross-sectional area, coil distance from the operating region, and coil aspect ratio; and repeating the computing, determining, and modifying steps until the percentage of ramping times in the distribution of ramping times that the selected minimum ramping time is exceeded is not more than the selected percentage of navigational direction changes.

A magnetic resonance imaging system comprising an electromagnet for generating a magnetic field in the vicinity of the a body for making a magnetic resonance image of a portion of the body and an x-ray image apparatus, comprising an x-ray image source and an x-ray image plate, for making an image of the portion of the body, at least the x-ray image plate being within the magnetic field generated by the electromagnet.

Thus the system of the present invention provides for effective magnetic guidance of magnetic medical devices within the body for performing medical procedures. The system is capable of providing magnetic fields of sufficient strength for orientation and even movement of magnetic medical devices, within a sufficiently large operating region to allow practical medical procedures to be completed with magnetic assistance. However, the magnets are arranged so that the operating region of the system can be positioned in any portion of the body. The system provides open access so that imaging plates can be interposed between the patient and the magnets to provide high-quality images of the operating region. The imaging apparatus can be moved independently of the magnets to provide the best possible views of the operating region.

These and other features and advantages will be in part apparent and in part pointed out hereinafter.

BRIEF DESCRIPTION OF THE DRAWINGS

FIG. 17 is a right side elevation view of the magnetic navigation system of the second embodiment;

FIG. 29 is an isometric view of the three electromagnet coils comprising the magnet assembly of the second embodiment;

FIG. 30 is a top plan view of the three electromagnetic coils comprising the magnet assembly of the second embodiment;

FIG. 31 is a front elevation view of the three electromagnetic coils comprising the magnet assembly of the second embodiment;

FIG. 32 is a right side elevation view of the three electromagnetic coils comprising the magnet assembly of the second embodiment;

FIG. 33 is a cross-sectional view of two of the electromagnetic coils taken along the plane of line 33—33 in FIG. 31;

Corresponding reference numerals indicate corresponding parts throughout the several views of the drawings.

DETAILED DESCRIPTION OF THE PREFERRED EMBODIMENTS

The First Embodiment

Figure 1:
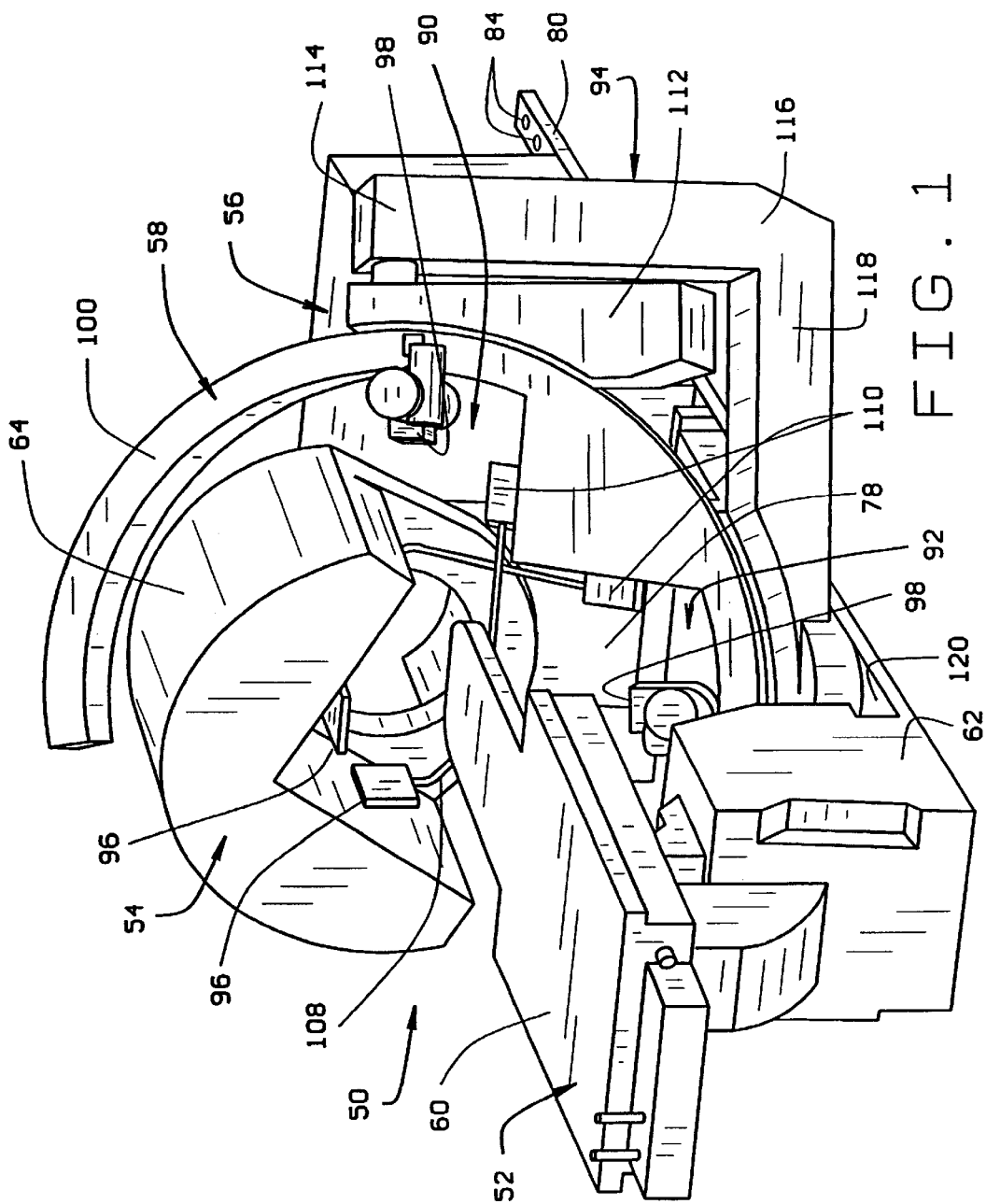
FIG. 1 is an isometric view of a first embodiment of a magnetic navigation system in accordance with the present invention.

A first embodiment of an inventive open field magnetic surgical system constructed according to the principles of this invention is indicated generally as 50 in FIG. 1. The system 50 comprises a patient support 52, a magnet assembly 54 on a moveable magnet support 56, and an imaging assembly 58.

The patient support 52 preferably comprises an elongate bed 60 mounted on a pedestal 62. The foot of bed 60 is oriented toward the front of system and the head of the bed is oriented toward the rear of the system. The head of the bed 60 is narrower than foot of the bed so that it can fit inside the magnet assembly 54 and accommodate the imaging devices of the imaging assembly 58. The bed 60 is preferably movable with respect to the pedestal 62, to allow the patient to be moved relative to the magnet assembly 54. The bed 60 can preferably be moved longitudinally forwardly and rearwardly and vertically upwardly and downwardly, and it can be rotated about its longitudinal axis.

The magnet assembly 54 comprises a housing 64 containing three magnets 66, 68, and 70. The magnets 66, 68, and 70 are preferably electromagnet coils and more preferably superconducting electromagnet coils 72, 74, and 76. Suitable power and cooling conduits are provided within the housing 64, as is known.

The magnet coils 72, 74, and 76 are arranged to provide a magnetic force within an operating region sufficient to move a magnetic medical device within that portion of a patient inside the operating region. This magnetic medical device may be, for example a magnet-tipped catheter, endoscope, or other elongate medical device or a magnet-tipped guidance for guiding an elongate medical device.

As best shown in FIGS. 7–10, coil 72 is arranged in a transverse plane with its axis 72' extending generally longitudinally, parallel to the axis of the patient support in this preferred embodiment, the coil 72 has an 26.090 inch outer diameter, a 19.010 inch inner diameter, and is 2.620 inches thick, carrying up to 100 amperes at 11.7 kA/cm$^2$. Coils 74 and 76 are similar in construction and preferably oriented in mutually perpendicular planes that are perpendicular to the plane of coil 72. Each of the coils 74 and 76 has an outside diameter of 21.826 inches, an inside diameter of 15.750 inches, and is 2.850 inches thick, carrying up to 100 amperes at 11.7 kA/cm$^2$. The faces of the coils 74 and 76 are spaced 11.9 inches from the axis of the coil 72, and the face of the coil 72 is spaced 12.75 inches from the axes 74' and 76' of the coils 74 and 76. The edges of coils 74 and 76 are spaced 1.88 inches from the edge of coil 72, and coils 74 and 76 are 1.45 inches apart at their closest points. The sizing and spacing of the magnet coils is described below.

The magnet coils 72, 74, and 76 are preferably arranged in mutually perpendicular planes such that the axes 72', 74', and 76' of the coils intersect at a point in the center of the operating region.

The magnet assembly 54 is preferably mounted on a moveable magnet support 56 with an arm 78, such that the magnet assembly can rotate about a longitudinal axis parallel to the longitudinal axis of the bed 60. The magnet assembly can preferably turn about 20° in either direction. This movement helps prevent shading of the imaging beam in certain circumstances. Of course, the magnet assembly could be fixedly mounted, if desired, and further could be fixedly mounted in a different orientation from that shown in the figures, for example below the patient support 52 to facilitate urological and GI uses of the system.

Figure 3:
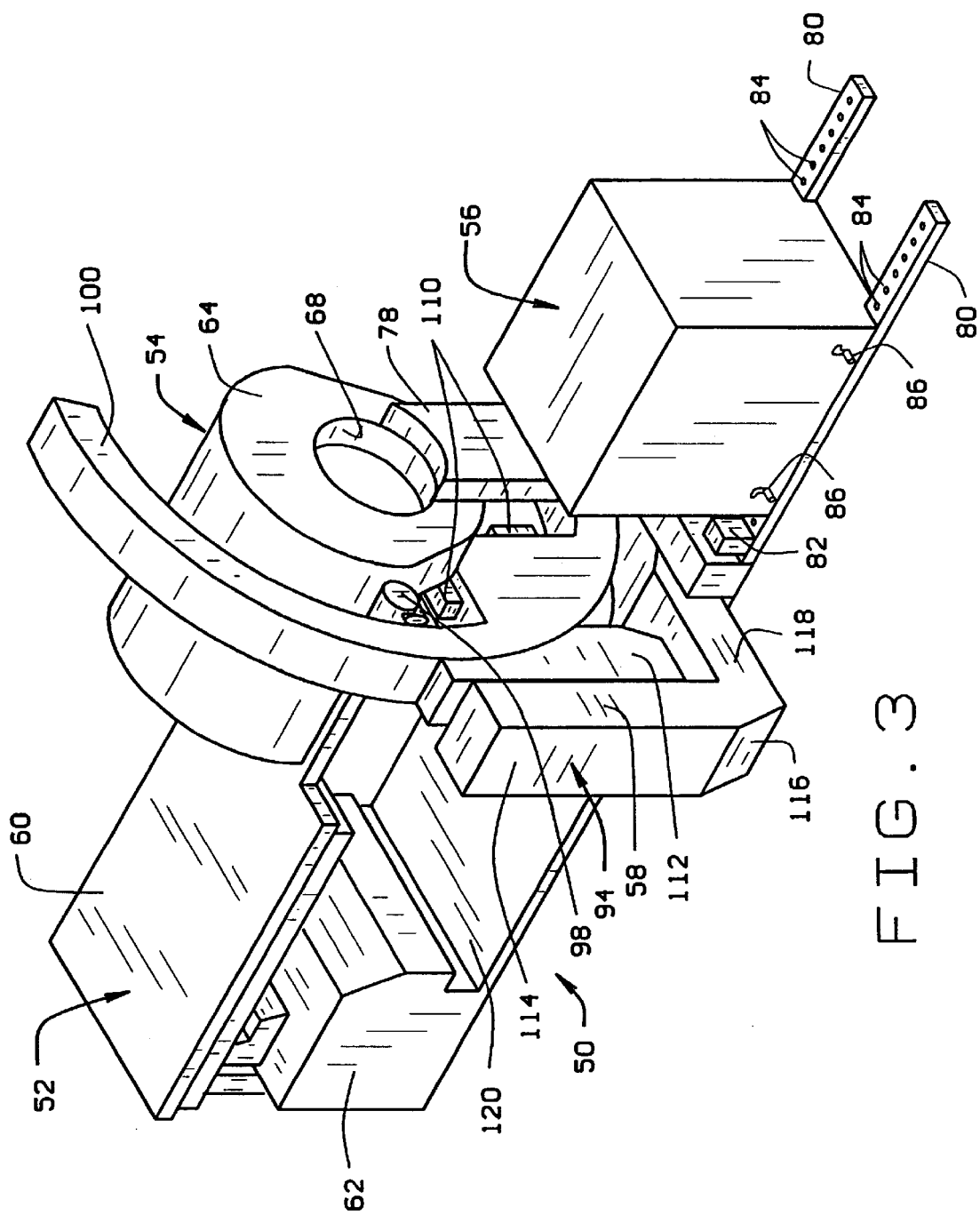
FIG. 3 is an isometric view from the rear of the system of the first embodiment.

The magnet support 56 contains power supply and coolant for the coils 72, 74, and 76. Power and coolant are communicated to the coils in housing 64 through arm 78. As shown in FIG. 3, the magnet support 56 is slidably mounted on tracks 80 to move forwardly and rearwardly (toward and away from the patient support). Stops 82 on the tracks 80 restrict forward motion of the magnet support 56. There are a plurality of holes 84 longitudinally spaced along the tracks 80. The magnet support 56 has locking pins (not shown) controlled by locking handles 86 to engage the holes 84 and lock the magnet in accurately located positions. Instead of, or in addition to, this locking mechanism, some other positioning mechanism such as a motorized or servo-controlled mechanism can be provided. This allows the position of the magnet assembly 54 to be automatically controlled by an external controller or computer.

The housing 64 preferably has an opening 88 aligned with the central opening of the coil 72, so that a portion of the patient support and/or the patient thereon can extend through the housing so that the desired portion of the patient's body can be positioned within the operating region of the magnet assembly 54.

The imaging assembly 58 comprises at least one imaging device, and in the preferred embodiment two imaging devices 90 and 92, mounted on a C-arm support 100 of C-arm 94. Such supports are made, for example, by General Electric Co. of Syracuse, N.Y. The imaging devices 90 and 92 are preferably arranged perpendicular to each other to provide bi-planar imaging in mutually perpendicular planes. Each of the imaging devices 90 and 92 comprises an imaging plate 96 and an imaging beam source 98. In this preferred embodiment the imaging plates 98 are amorphous silicon imaging plates, known as LAST plates available from Varian, Palo Alto, Calif. These plates 96 are not affected by the presence of magnetic fields, such as those caused by the magnet coils 70, 72, and 74. The imaging beam sources 98 are preferably X-ray sources. Of course some other imaging beam and imaging plate could be used if desired.

As shown in the Figures, C-arm 94 comprises a C-shaped support 100 on which the X-ray sources 98 of the imaging devices 90 and 92 are mounted. The C-shaped support 100 has a wedge shaped block 102 having perpendicular faces 104 and 106 which arms 108, each mounting one of the imaging plates 96, extend. The arms 108 are hollow, providing a protected path for electrical wiring to the imaging plates 96. The arms 108 are preferably attached to blocks 110 that can move on their respective faces 104 and 106, to permit adjustment of the positions of the imaging plates 96.

The C-shaped support 100 is mounted on body 112, and moves about its circumference relative thereto so that the C-shaped support turns about its central axis. The body 112 is rotably mounted to the vertical leg 114 of a generally L-shaped bracket 116. The body 112 can rotate relative to the L-shaped bracket 116 about a generally horizontal axis. The horizontal leg 118 of the generally L-shaped bracket 116 is pivotally mounted to the base 120 of the system so that the generally L-shaped bracket pivots about a generally vertical axis.

Figure 4:
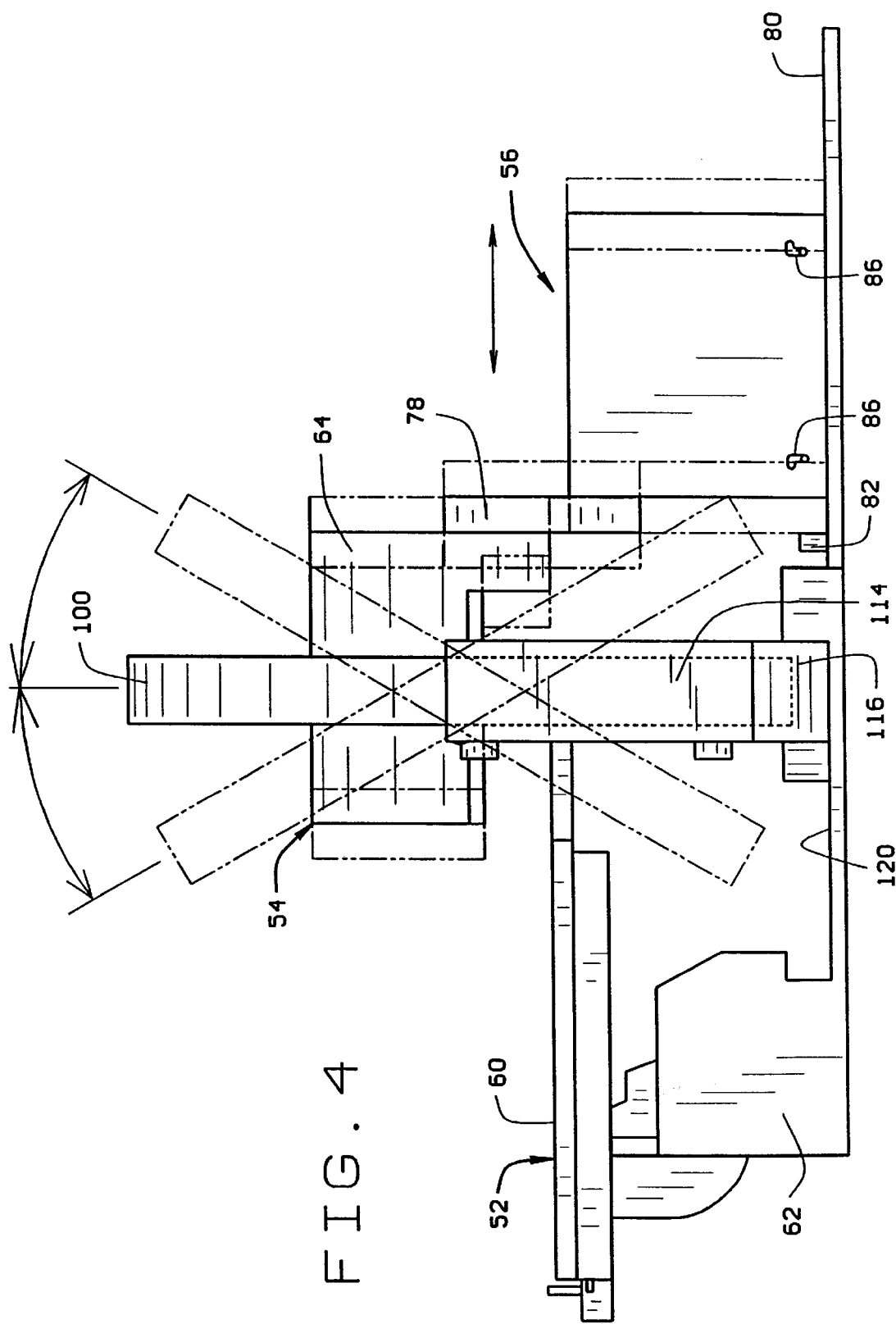
FIG. 4 is a right side elevation view of the system of the first embodiment, showing the range of angular motion of the imaging system about a transverse horizontal axis.
Figure 5:
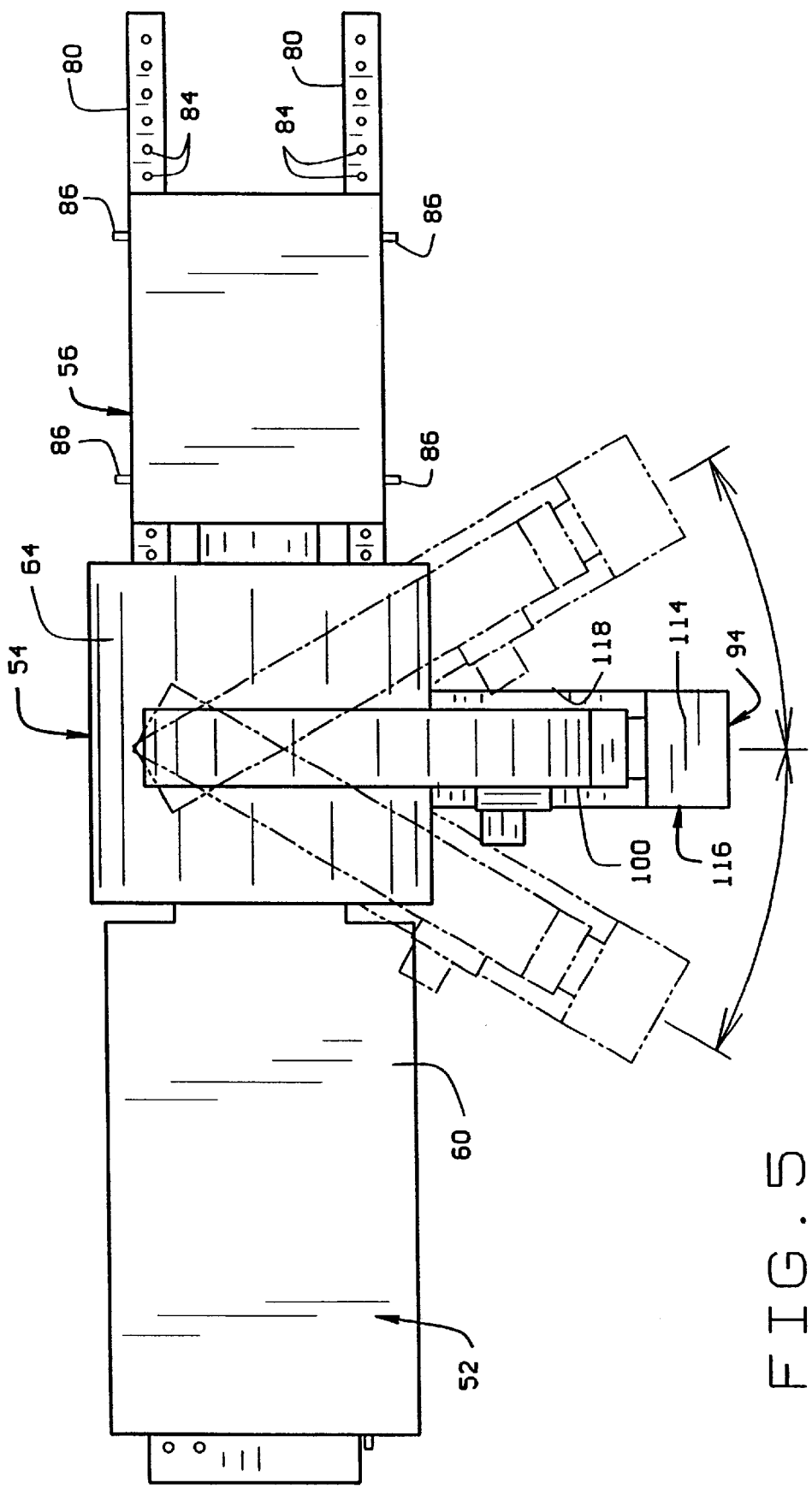
FIG. 5 is a top plan view of the system of the first embodiment showing a range of angular motion of the imaging system about a vertical axis.
Figure 6:
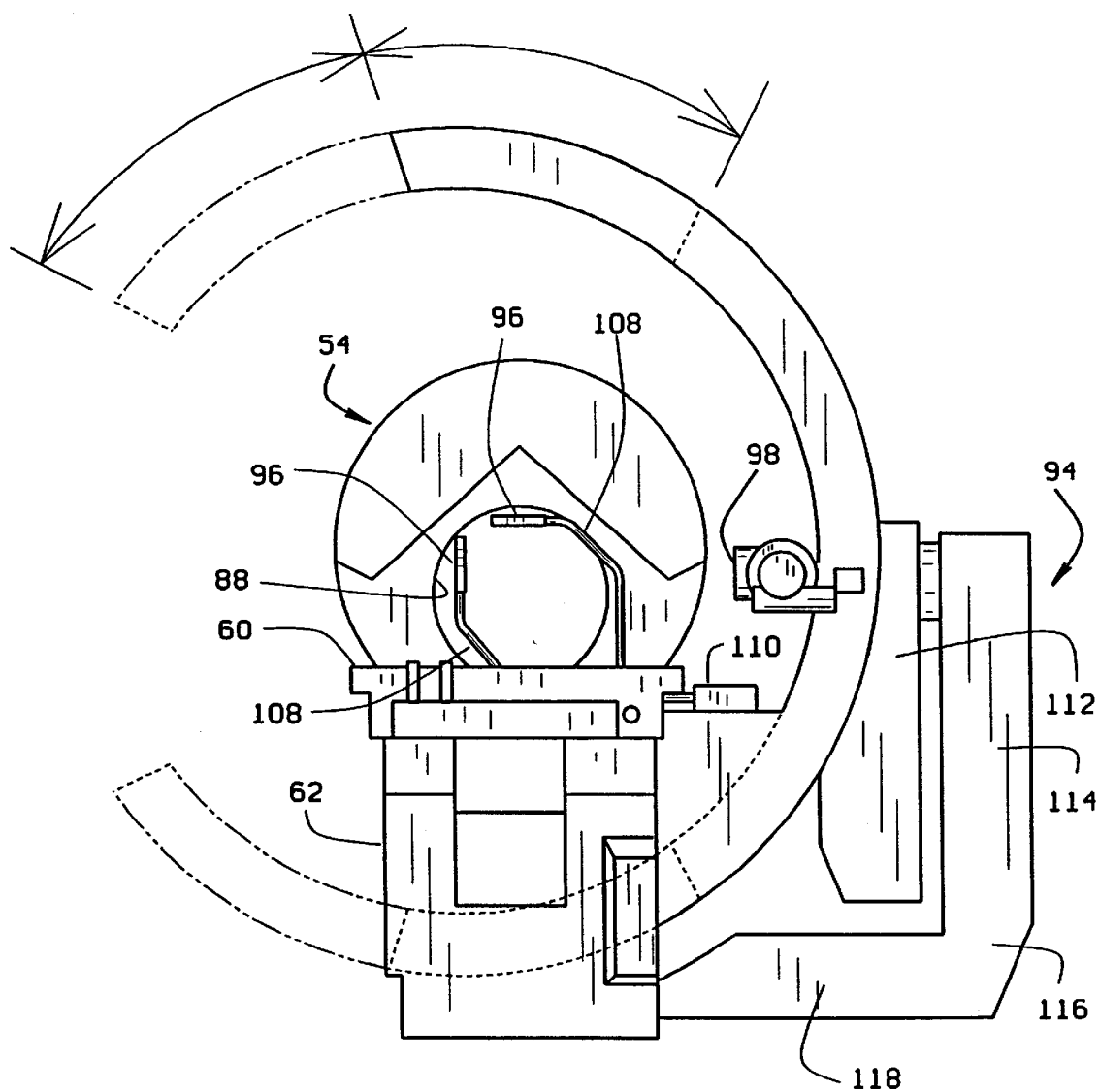
FIG. 6 is a front elevation view of the system of the first embodiment showing a range of angular motion of an arcuate section of the imaging assembly about a horizontal axis.
Figure 7:
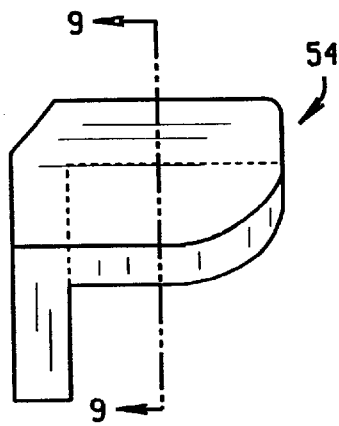
FIG. 7 is a left side elevation of the structure for supporting the electromagnetic coils of the first embodiment.
Figure 8:
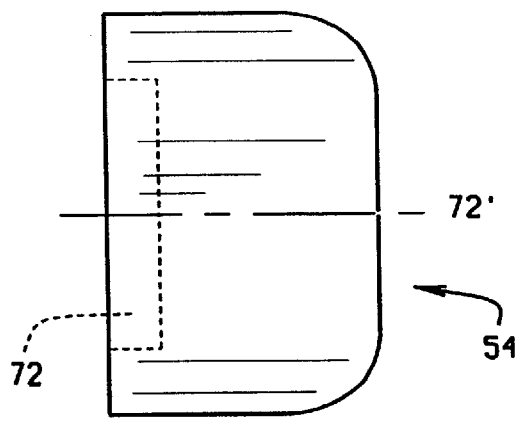
FIG. 8 is a top plan view of the structure for supporting the electromagnetic coils.
Figure 9:
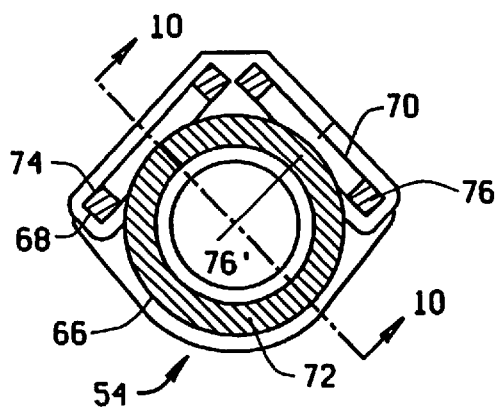
FIG. 9 is a vertical cross-sectional view of the structure for supporting the electromagnetic coils, taken along the plane of line 9—9 in FIG. 7.
Figure 10:
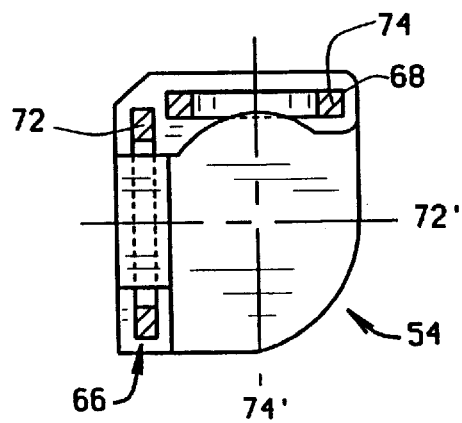
FIG. 10 is a cross-sectional view of the structure for supporting the electromagnetic coils, taken along the plane of 10—10 in FIG. 9.

The C-arm 94 thus allows the imaging devices 90 and 92 to be rotated about three mutually perpendicular axes. These axes preferably intersect, and their intersection is preferably in the operating region of the magnet assembly 54, and more preferably their intersection coincides with the intersection of the axes 72', 74', and 76' of the magnet coils 72, 74, and 76. The imaging devices 90 and 92 rotate about a first axis when the C-shaped support 100 turns relative to the body 112 (see FIG. 6). The C-shaped support 100 can preferably rotate clockwise and counter clockwise over a range of about 90°. The imaging devices 90 and 92 rotate about a second generally horizontal axis when the body 112 rotates relative to the L-shaped bracket 116 (see FIG. 4). The body 112 can preferably rotate about 30° forwardly and rearwardly with respect to the L-shaped bracket 116. The imaging devices 90 and 92 rotate about a third generally vertical axis when the L-shaped bracket 116 rotates relative to the base 120 (see FIG. 5). The L-shaped bracket 116 can preferably rotate about 30° forwardly and rearwardly with respect to the base 120.

Figure 2:
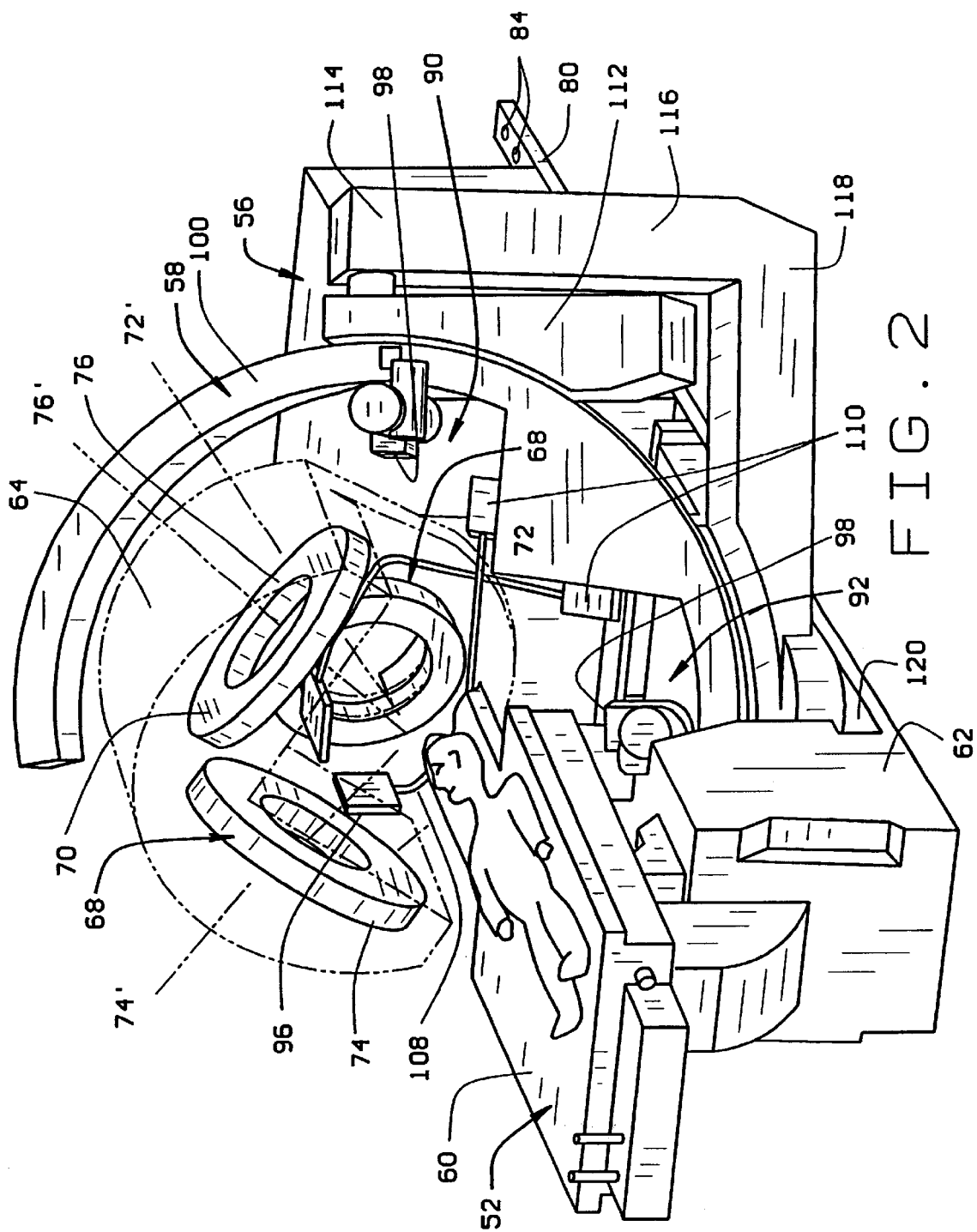
FIG. 2 is another isometric view of the system the first embodiment in showing the positions of the magnetic coils and a patient on the patient support.
Figure 2A:
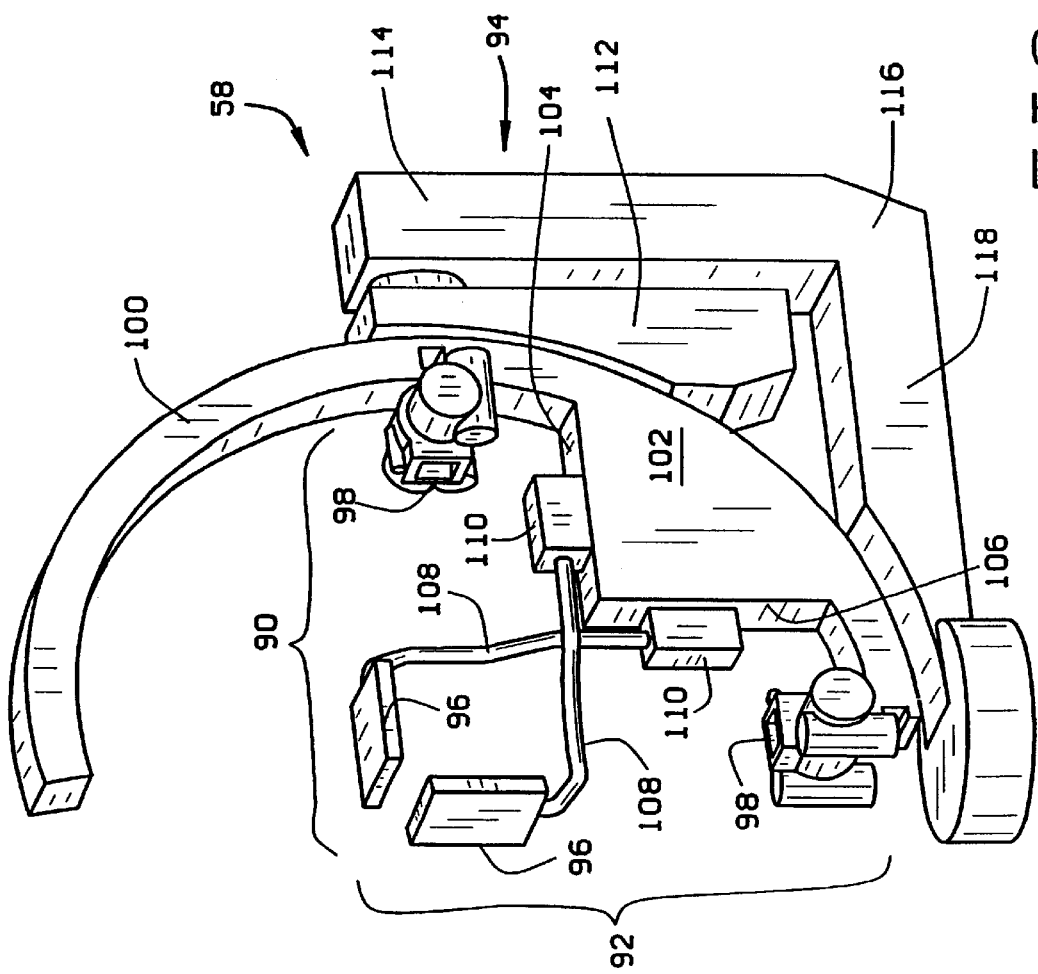
FIG. 2A is an isometric view of the imaging assembly on the C-arm structure of the system of the first embodiment.

As best shown in FIG. 2A the imaging apparatus 58 provides bi-planar imaging of the portion of the patient's body inside the operating region of the magnet assembly 54. The support arms 108 are configured to clear the patient and the head of the bed, and support the imaging plates 96 in the space between the operating region and the magnet coils 72, 74, and 76, of the magnet assembly 54 while maintaining the imaging plates aligned with their respective imaging beam sources 98. The imaging devices 90 and 92 can be moved around the operating region to accommodate movement of the magnet assembly 54 and to provide the most advantageous views of the operating region so that the surgeon can see the navigation of the magnetic medical device.

The magnet coils 72, 74, and 76 provide a controllable magnetic field inside that portion of a patient within the operating region of the magnet assembly 54. The coils 72, 74, and 76 provide a magnetic field of at least about 0.1 Tesla, and in the preferred embodiment at least about 0.3 Tesla. The imaging devices 90 and 92 provide bi-planar imaging of the operating region. The imaging plate 96 and the imaging beam source 98 are positioned on opposite sides of the operating region, with the imaging plates disposed between the operating region and the magnet coils 72, 74, and 76.

Figures 11, 12:
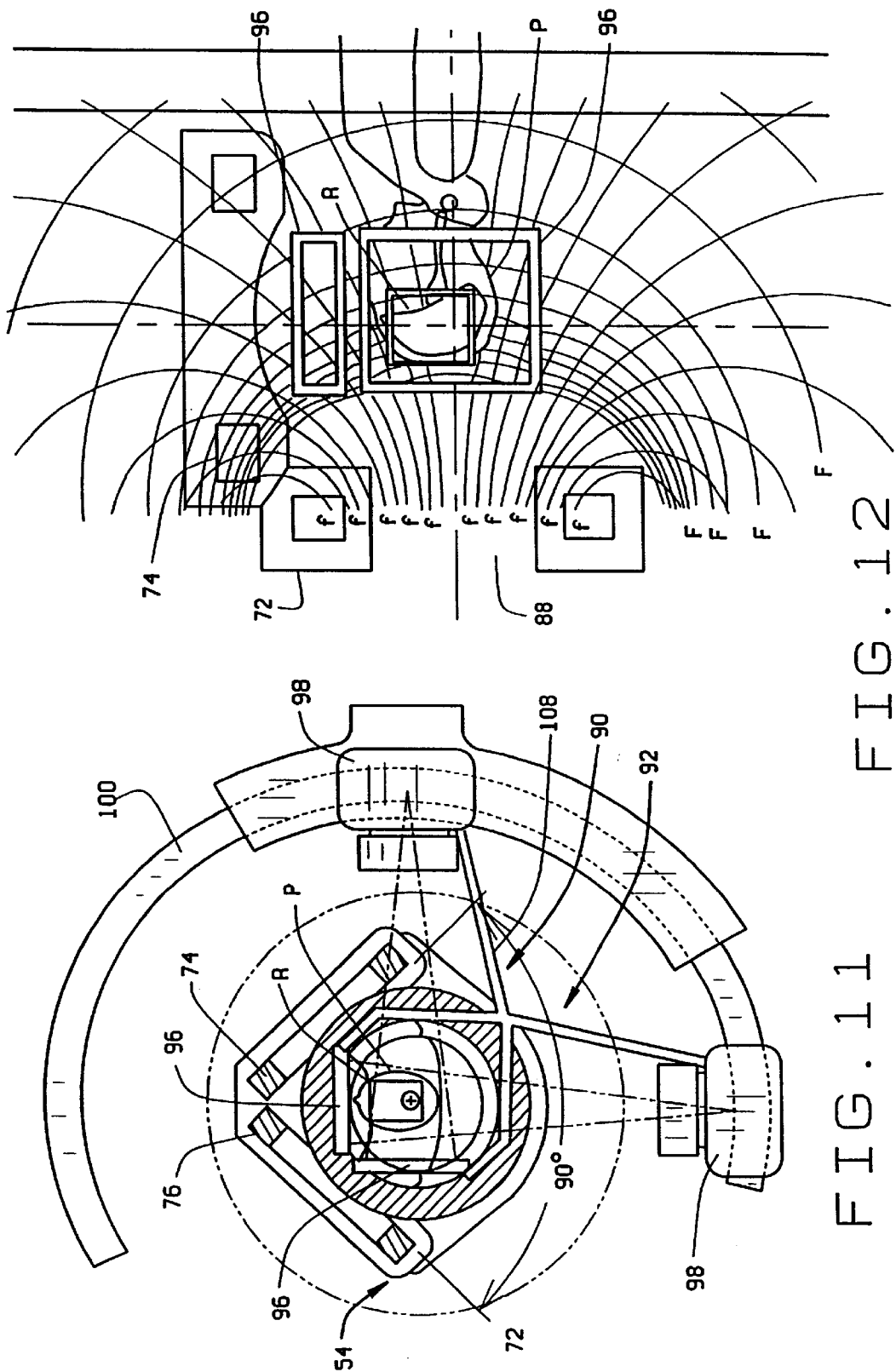
FIG. 11 is a rear end elevation view of the electromagnetic coils and the imaging system.
FIG. 12 is a left side elevation view of the electromagnetic coils with a patient therein showing the magnetic field lines of the axial coil, along with lines of constant magnetic field strength.
Figure 13:
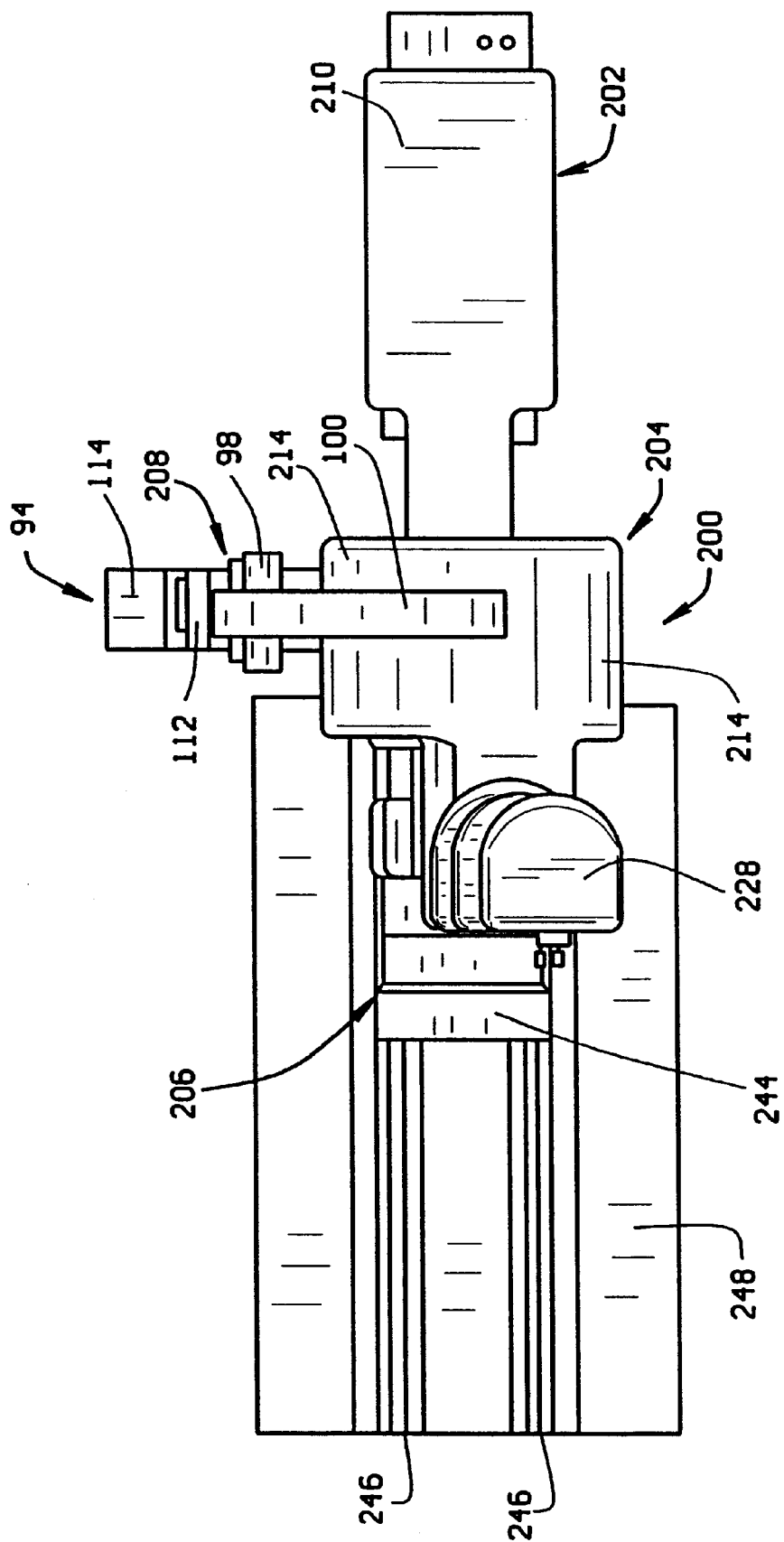
FIG. 13 is a top plan view of a second embodiment of a magnetic navigation system constructed according to the principles of this invention.
Figure 14:
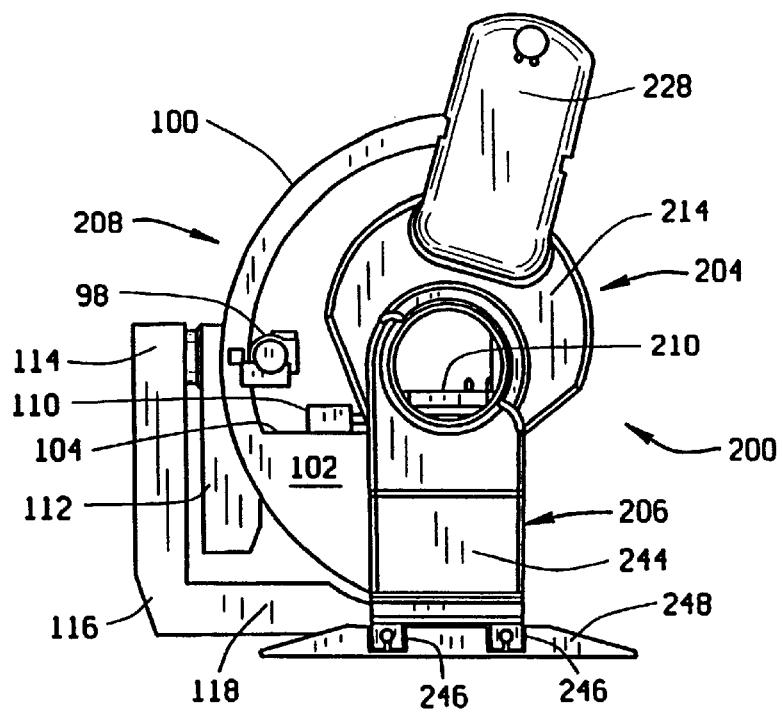
FIG. 14 is a rear end elevation view of the magnetic navigation system of the second embodiment.
Figure 16:
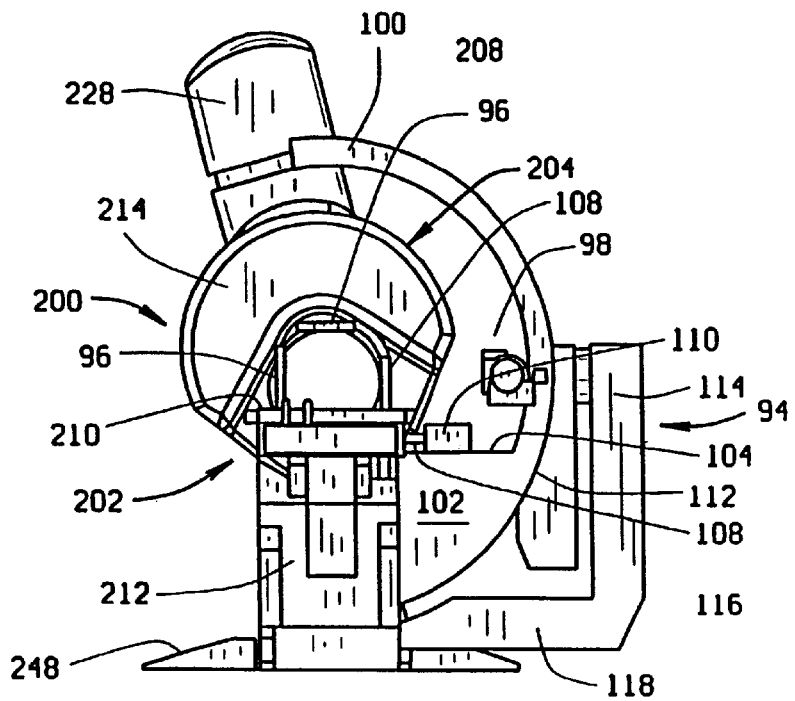
FIG. 16 is a front end elevation view of the magnetic navigation system of the second embodiment.
Figure 15:
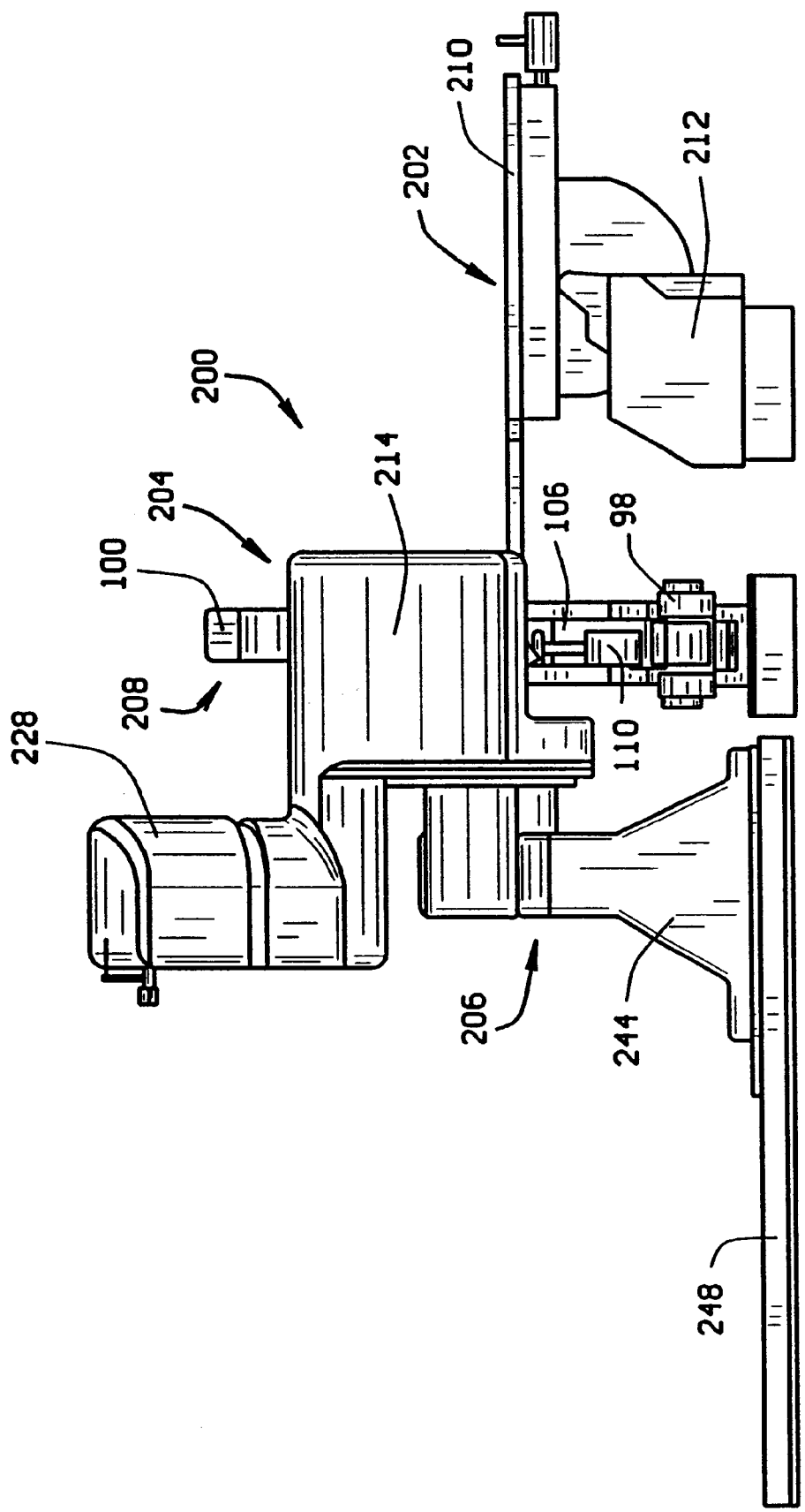
FIG. 15 is a left side elevation view of the magnetic navigation system of the second embodiment.
Figure 18:
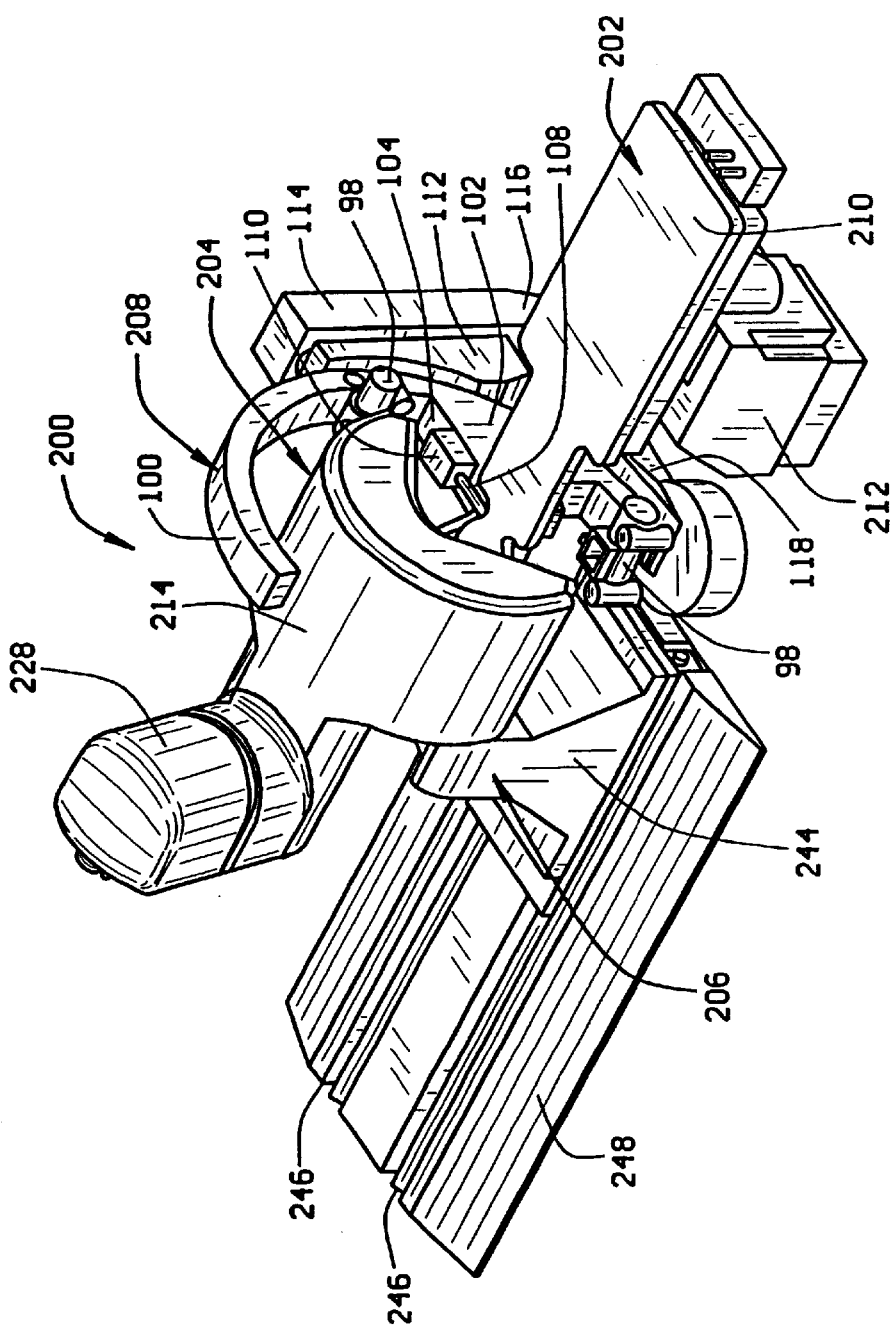
FIG. 18 is an isometric view of the magnetic navigation system of the second embodiment.

FIG. 11 is a partial representation of the apparatus shown in FIGS. 1–5, with portions omitted to show the operational relationship between the electromagnetic coils 72, 74, 76, the imaging tubes 98, the imaging plate supports 108, and the imaging plates 96. Also shown is the passageway 88 through which a physician has access to an operating region R in which the surgical procedure is taking place in patient P. As explained above, the passageway 88 allows portions of the patient to extend through the magnet assembly in order to bring selected portions of the patient into the operating region. Although FIG. 11 is not drawn to scale, a comparison of FIG. 11 shows that arcuate support 100, on which the imaging devices 90 and 92 are mechanically coupled, may reorient those mechanically-coupled apparatuses about the various axes with three degrees of freedom to provide different medically useful views of operating region R within the patient P.

Sizing and Locating the Electromagnet Coils

The method by which the size and location of the coils can be selected is as follows: It is to be understood that use of the same method, with different compromises or initial assumptions, may result in a system having coils of somewhat different sizes and locations, but still within the principles of this invention.

Using the Biot-Savart Law, it is possible to calculate the magnetic field everywhere for a coil having a given shape, size, and total number of ampere-turns. To arrive at the particular combination of size and location described above, the inventors started with the assumption that three coils would provide the best compromise between being too large and too close to provide a needed internal exclusion volume for imaging equipment and beams, while not being too weak to provide the needed strength in a given operating region or procedure volume inside the patient. The three coil choice follows from experience with six coil systems, and, in accordance with the invention, provides much more freedom for physicians and imaging.

The inventors also intended for the body-axis coil (coil 72 in the first embodiment), to be larger and to have a free air bore large enough for the patient's head, with clearance for tubes, etc., so that the patient's chest can be positioned within the operating region. It is also most convenient and economical for construction purposes and for calculating operating currents to have the three coils be orthogonal, and for the two transverse coils to be alike. Other non-orthogonal arrangements could be calculated, but would result in less efficient structural designs.

These qualitative requirements dictate the approximate size and shape of the three coils. If the coils are huge, they would provide great freedom for the imaging devices and for the surgeon, but the coil would be heavy, expensive and have long ramping times for field changes. If the coils are too small, they would interfere with the location and motion of the imaging plates 96. That is, the coils must be far enough from a central convergence point, the intersection of the three coil axes approximately centered in the operating region, that a pair of orthogonal imaging plates can move about the portion of the patient in the operating region, and not touch the coils, nor shadow each other's imaging x-ray beams. The dimensional details of the imaging equipment and beams, of the trial coil sizes and shapes, of the patient and the bed, etc., are put into a three-dimensional CAD program for interactive decision-making magnetic field determinations.

Added to this, the coils must be large enough, individually, that their near field lines do not bend severely in the operating region, which is centered near the intersection of their axes. Otherwise, it becomes difficult to attain the field strengths needed at the needed distances from the coils, for certain directions of the field.

An exact determination of the coil sizes and locations is achieved by iterative computer modeling in conjunction with the CAD plots. On a computer, a first trial size is chosen for the three coils of the set, and the fields are calculated at various angles and distances from the coil, assuming a current density (e.g., 14,000 Amperes per square cm) that is suitable for the superconducting coils of these strengths. From this choice, field lines and lines of equal field strength at full current for one coil (e.g., the axial coil, 72 in the first embodiment) are plotted to scale on a CAD drawing of the system with assumed coil location and with patient and imaging equipment in place.

FIG. 12 is an illustration of such a CAD drawing. The operating region R within a patient P is shown, as are magnetic field lines f generated by coil 72. Lines F representing contours of equal magnetic field strength are also shown. Locations of imaging plates 96 are also represented. The axial coil (72 in the first embodiment) is also shown in FIG. 12, although its magnetic field is not represented. (The orientation of coil 74 as shown in FIG. 12 is not the same as that shown in FIG. 1 and other figures.) The axes 72' and 74' and of coils 72 and 74, respectively, are also represented in FIG. 12.

Given a target field strength requirement, e.g., 0.3 Tesla, it can be determined, from the iterative computer modeling or by some other method, whether the individual coils have sufficient strength to cover, or nearly cover, the operating region, when appropriately combined. If the coils are too strong, the ramp time and weight will be too great, and their cross section can be reduced.

Each coil supplies most of the field strength for the direction along its axis. The general requirement of small field curvature for the field lines leads to the fact that the coils act predominantly independently for each axis. That is, orthogonal coils do not contribute an operatively significant field component along the direction of the axis of the other coils in the operating region. And, curved lines fail to achieve sufficient strength along bisecting planes between coils. The total field at any location in the operating region, and at any required angle, therefore, will be, for purposes of magnetically-assisted surgery, the sum of the individual fields from each of the three coils. While this "vector sum" model which assumes straight field lines is only approximately correct, a computer can make accurate, detailed calculations of the total fields of the system with any given set of currents. A final determination of meeting field requirements in the operating region involves only modest changes from the trials just described. The final determination of coil sizes and locations, subject to the general considerations stated above, uses a computer program to calculate the magnetic fields and resultant ramping times as follows.

The operating region can be broken into small segments or "nodes," for example, of about 20 along each side, so that a cubical-shaped operating region would have about 8,000 nodes. For about 20 random directions, in each node, the computer calculates the three coil currents needed to provide the required magnetic field strength at each direction, should the operating point be in the center of that node. Consequently, a total of 20×8,000 calculations are made to provide this sampling of the total operating region. (Only two angles are needed to specify any direction in space, for example, a polar and an azimuthal angle. Therefore, there are only three unknown currents in each calculation, and the magnetic field strength and direction constitute three unknowns, so the calculation is a simple matrix solution. Information about such matrix calculations is provided in patent application Ser. No. 08/920,446, filed Aug. 29, 1997, on "Method and Apparatus for Magnetically Controlling Motion Direction of a Mechanically Pushed Catheter," incorporated by reference herein in its entirety.

In using these calculations, it is often important to the physician in a particular application to be able to make use of a statistical statement about the distribution of coil currents, and consequently, the ramping time. For the purpose of determining the time needed for ramping, the maximum current of each set, is chosen in a sequence of turns in navigating to a target, and a model of the ramping needs is used. In one application, the essential ramping sequence has the following steps: (1) determine the previous field direction at the magnetic object location, (2) determine the desired new direction and the angle of the change, (3) using knowledge of the field needed to make a turn of this magnitude, set the new field direction and magnitude, (4) execute the new ramp, and (5) upon completion of the ramp and turn, ramp the current down.

Each of these five-step sequences can be evaluated for the total ramp-up, ramp-down time. The computer can do the estimates for each of the above-stated 160,000 cases, and perform plots of either the overall probability distribution of ramp times, or it can plot binned probabilities for turns of 0–10°, 10–20°, etc. Such plots can inform the surgeon of the time needed for a given angle of turn. And, with an intuitive display, such as a thermometer type representation on a screen, the surgeon can quickly decide whether magnetic assist is necessary or useful on any given turn, thereby increasing the efficiency and effectiveness of the overall procedure.

When the optimum compromise of coil size, location and coil power is determined, the dimensions and magnetic requirements are met, the design goes to a succeeding stage. From mechanical application of the Biot-Savart law, it is possible to calculate the stresses on each coil due to the interaction of currents in it and in the other coils. Textbooks (e.g., Foundations of Electromagnetic Theory, Reitz, Milford, and Crysty, $3^{rd}$ Ed., page 166) give equations that may be used to calculate the vector differential interaction force $d^2F$ between a differential length of a first coil, $dl_1$, carrying current $I_1$, and a differential length of a second coil, $dl_2$, carrying current $I_2$. These can be integrated or approximately summed. In the latter case, subtended angles of ten degrees might, for example, be chosen for each coil and the appropriate interactions vector summed. It would be useful in such a case to find the total force dF on each segment subtending 10 degrees of the first coil from the complete 360 degrees of each of the other two coils (the second coil and a third coil). This complete procedure is able to handle any given cross section of these circular coils, when used in a typical finite element program such as "Maxwell EM" by Ansoft Corporation of Pittsburgh, Pa.

Then the three components of dF are entered into a finite element analysis program "FEA" dealing with stresses and forces, e.g. "pro/MECHANICA"®, Parametric Technology Corp., Waltham, Mass., which can be used by one skilled in the art on any inputted structure supporting the three coils. An individual coil force is transmitted from its surround, a "bobbin," to the supporting structure. In one simple but not preferred embodiment, three plates are welded together, each supporting one of the coils in the appropriate location. The results of calculation are often plotted as colored graphs, where regions of different stresses in the support structure (responding to the magnetic forces) are shown in different color. In addition, the program can determine deflections by summing reaction deflection to the stresses in individual elements of the structures. Then the designer tries different support struts which can alleviate excessive stresses or deflections in the first, simpler trial design. By an iterative process, and standard experience in mechanical design, the designer arrives at design shapes and/or structure details that minimize the overall weight of the structure, while exhibiting no excessive stresses and deflections.

In addition to the structural support and strength, the coil mounting system for superconducting systems must consider the cryogenic materials and transfer of heat and cryogens. Those skilled in the art have methods and programs to calculate heat transfer. They also have methods for most efficiently arranging insulation, vacuum spaces, intermediate heat shields, and ducting for liquid cryogen transfer, as well as cold gas exit, if the system is not recondensing and recirculating.

Several overall cryogenic systems in common practice are suitable for the practice of this invention. One such system simply uses liquid helium to cool the superconducting coils. The liquid helium evaporates and goes out as a gas. This system usually employs a 77° Kelvin shield attached to a liquid nitrogen reservoir. Another method uses a cryogenic cooler that cools an object down to the approximately 4.5° Kelvin needed to maintain superconducting wires in the superconducting state. This cryogenic cooler may either be attached solidly to the coil bobbin or it may, for flexibility, be coupled with liquid helium, which may either be totally enclosed or may need occasional replenishing. A cryogenic cooler may be used to cool a shield to intermediate temperatures. The cryogenic cooler may be attached solidly to the shield, or with a gas coupling, such as liquid neon. Cryogenic coolers have been designed to have two or more stages so as to supply more heat removing power at the higher, intermediate temperatures, and a lower cooling rate at the liquid helium temperatures. The selection of which system to use depends upon both economical and technical features, because cryocoolers are, at present, relatively expensive. Liquid helium is also expensive, however, and both space and weight are important considerations. Therefore, recirculating systems, which can be smaller and lighter, may be preferred.

As is known, the coils may have a split or two piece construction to better accommodate thermal contraction upon cooling, and to facilitate coolant.

The Second Embodiment

A second embodiment of an inventive open field magnetic surgical system constructed according to the principles of this invention is indicated generally as 200 in FIGS. 13–24. The system 200 is similar in construction to the system 50, and comprises a patient support 202, a magnet assembly 204 on a moveable magnet support 206, and an imaging assembly 208.

The patient support 202 preferably comprises an elongate bed 210 mounted on a pedestal 212. The foot of the bed 210 is oriented toward the front of the system and the head of the bed is oriented toward the rear of the system. The head of the bed 210 is narrower than the foot of the bed so that it can fit inside the magnet assembly 204 and accommodate the imaging devices of the imaging assembly 208. The bed 210, is preferably moveable with respect to the pedestal 212 to allow the patient to be moved relative to the magnet assembly. The bed can be moved into and out of the system; raised and lowered, and rotated about its longitudinal axis. Other movements can be provided to facilitate positioning the patient relative to the operating volume of the magnet assembly.

The magnet assembly 204 comprises a housing 214 containing three magnets 216, 218, and 220. The magnets 216, 218, and 220 are preferably electromagnetic coils, and more preferably superconducting electromagnetic coils 222, 224, and 226. The housing 214 includes a jacket 228 containing suitable power and cooling apparatus to operate the superconducting coils.

The magnet coils 222, 224, and 226 are arranged to provide a magnetic force within the operating volume sufficient to move a magnetic medical device within that portion of a patient inside an operating region.

As best shown in FIGS. 29–33 the magnet coils 222, 224, and 226 are preferably arranged in three mutually perpendicular planes such that the axes of the three coils intersect generally in the center of the operating region. Coil 222 is arranged in a transverse plane with its axis extending generally longitudinally, parallel to the longitudinal axis of the patient support 202. The coil 222 is wound around a bobbin 230 that is secured to a plate 232. In this preferred embodiment, the coil 222 has a 28.2 inch outer diameter, a 21.06 inch inner diameter, and is 4.47 inches thick.

Coils 224 and 226 are similar in construction and are preferably oriented in mutually perpendicular planes that are perpendicular to the plane of coil 222. Each of the coils 224 and 226 has an outside diameter of 26.48 inches, an inside diameter of 20.23 inches, and is 5.69 inches thick. The faces of the coils 224 and 226 are spaced 13.81 inches from the axis of the coil 222, and the face of the coil 222 is spaced 13.78 inches from the axes of the coils 224 and 226. Coil 224 is wound around a bobbin 234 that is secured to plate 236. Coil 226 is wound around bobbin 238 that is secured to plate 240. The plates 232, 236 and 240 are secured together to form a self-supporting structure capable of withstanding the forces generated by the magnetic fields of the coils. The housing 214 preferably has an opening 242 therein aligned with the central opening in coil 222 so that a portion of the patient support and/or the patient can extend therethrough, to bring the desired portion of the patient within the operating region of the magnet assembly 204.

The housing 214 is preferably mounted on a stanchion 244, which in this second embodiment forms the magnet support 206. The housing 214 preferably can pivot relative to the stanchion 244 about a longitudinal (front to back) horizontal axis. The housing 214 can preferably pivot 20° from the center (See FIG. 24) toward the left (See FIG. 21A) and the right (See FIG. 23). The bottom of the stanchion 244 is slidably mounted in tracks 246 in the base 248 of the system 200. Thus the stanchion 244 (and the housing 214) can be moved forward (toward the patient support 202) and rearward (away from the patient support).

Figure 19:
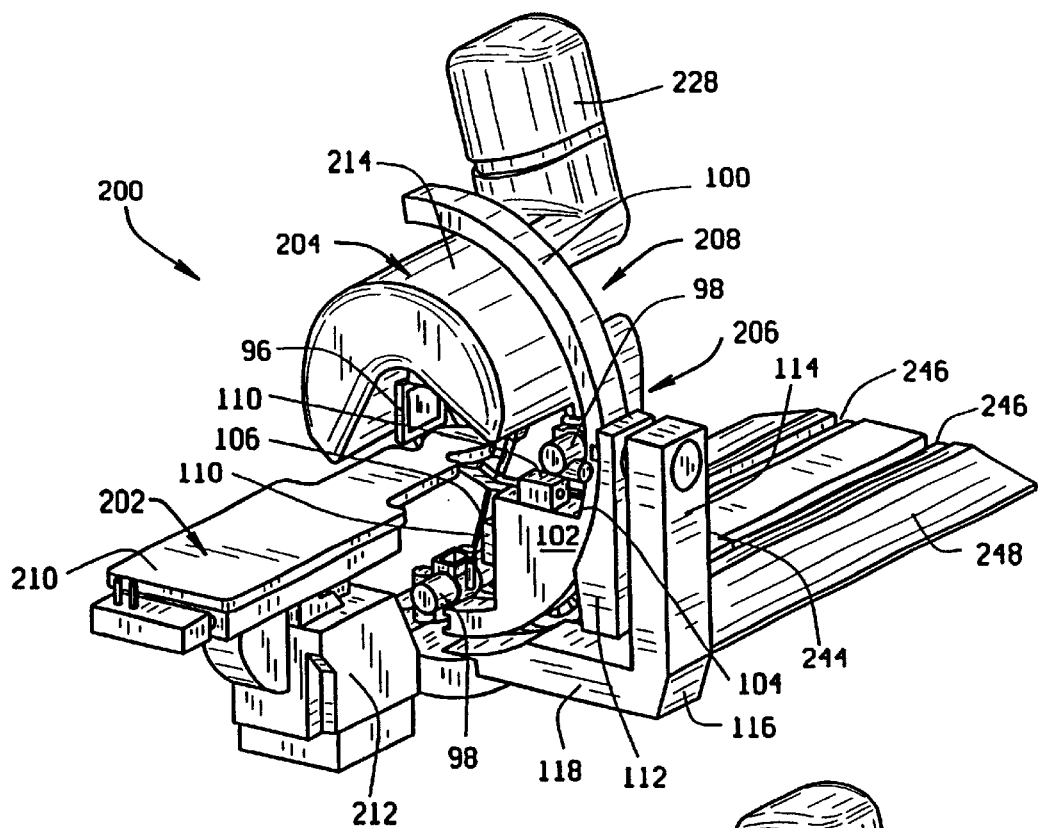
FIG. 19 is an isometric view of the magnetic navigation system of the second embodiment, showing the C-arm for supporting the imaging apparatus in its neutral position.
Figure 20:
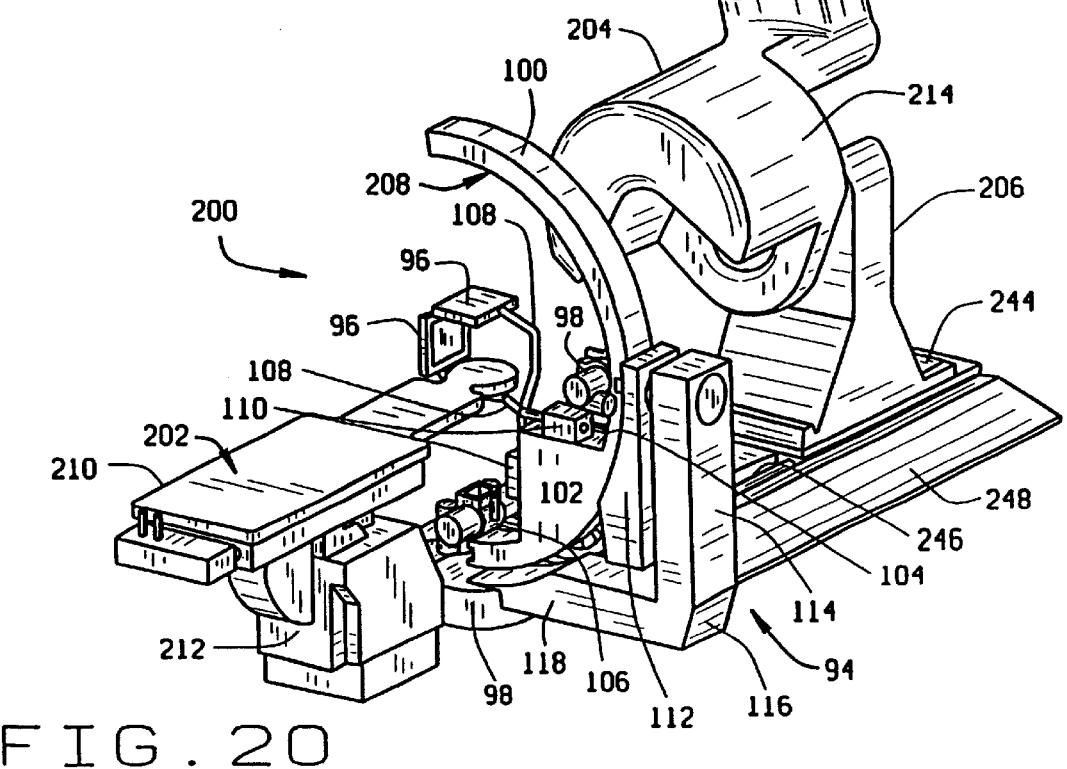
FIG. 20 is an isometric view of the magnetic navigation system of the second embodiment, showing the magnet assembly retracted.
Figure 21A:
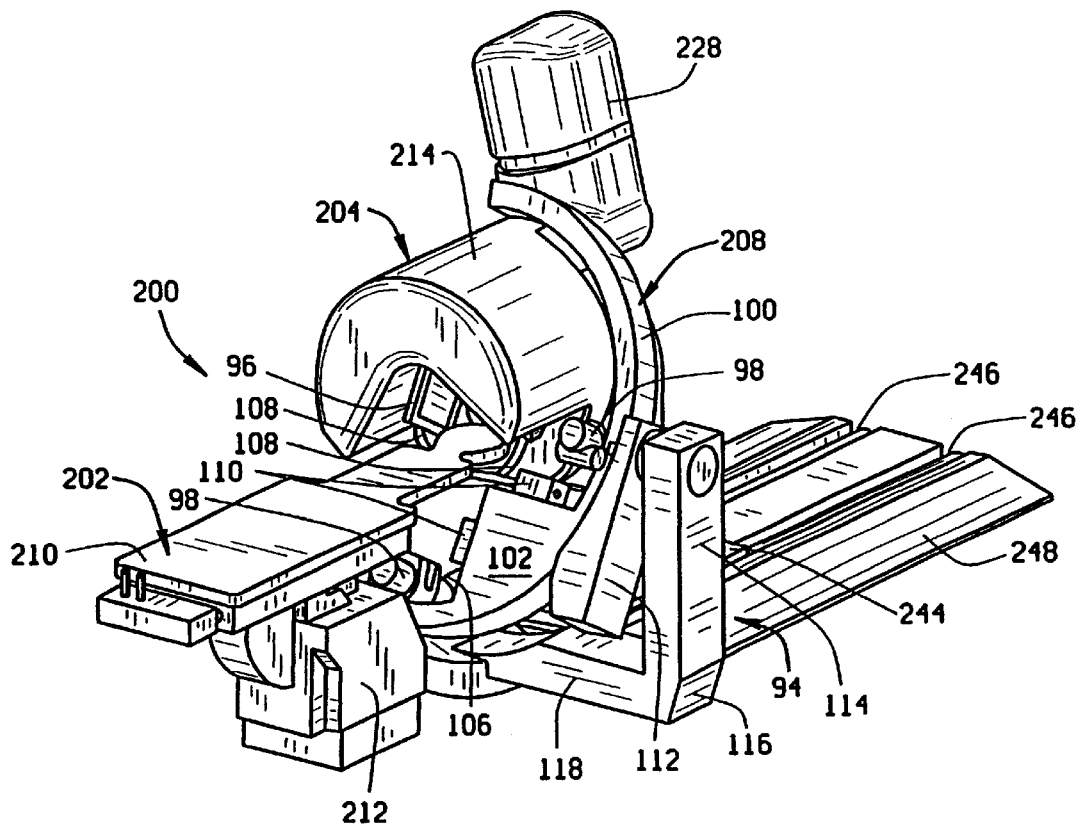
FIG. 21A is an isometric view of the magnetic navigation system of the second embodiment, showing the C-arm rotated +30° about a transverse horizontal axis.
Figure 21B:
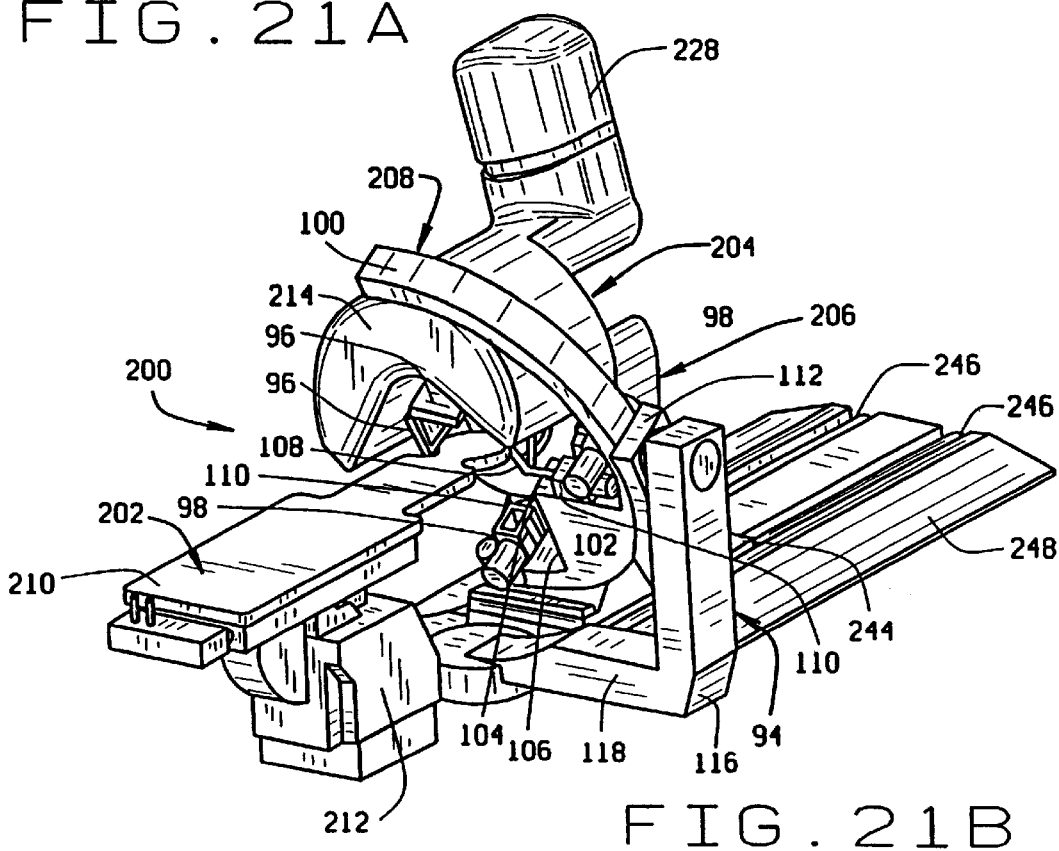
FIG. 21B is an isometric view of the magnetic navigation system of the second embodiment, showing the C-arm rotated −30° about a transverse horizontal axis.
Figure 22A:
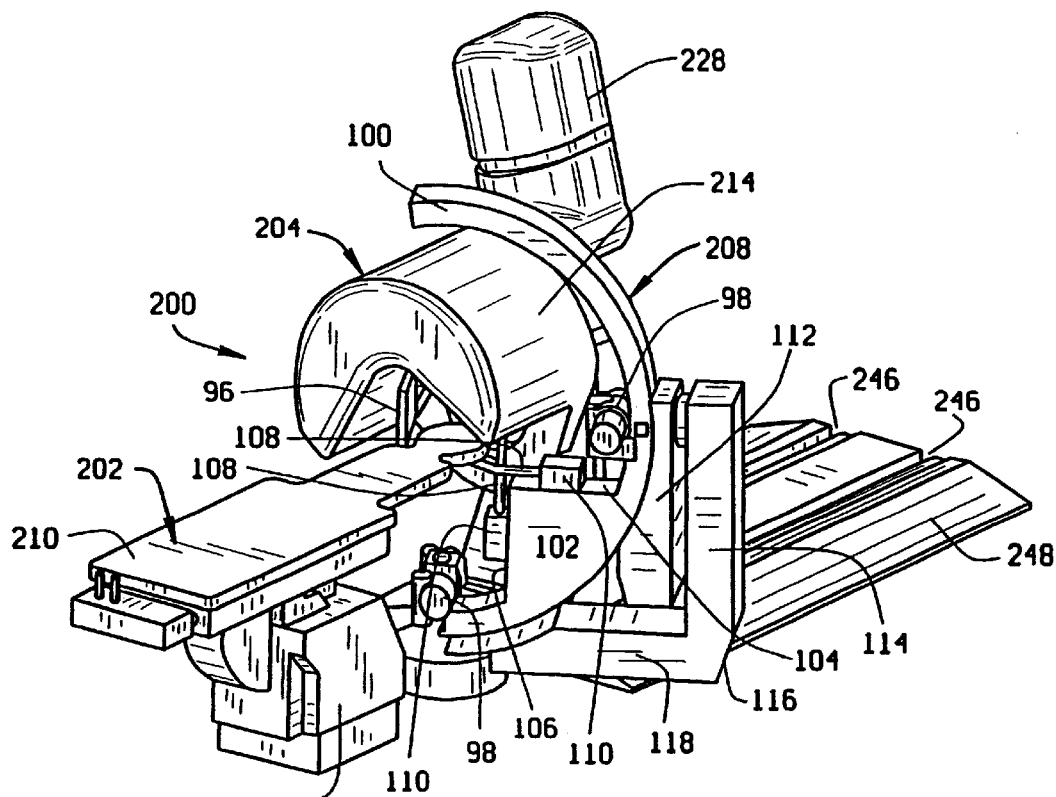
FIG. 22A is an isometric view of the magnetic navigation system of the second embodiment, showing the C-arm rotated +30° about a vertical axis.
Figure 22B:
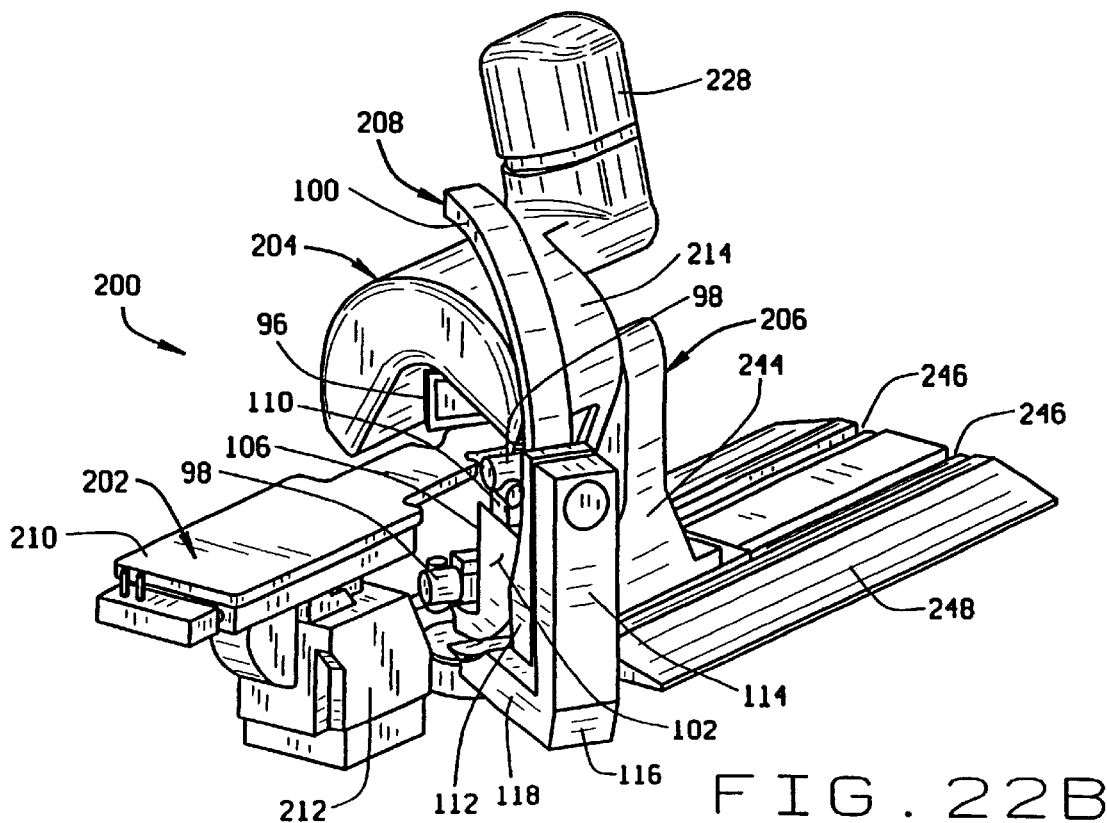
FIG. 22B is an isometric view of the magnetic navigation system of the second embodiment, showing the C-arm rotated −30° about a vertical axis.
Figure 23:
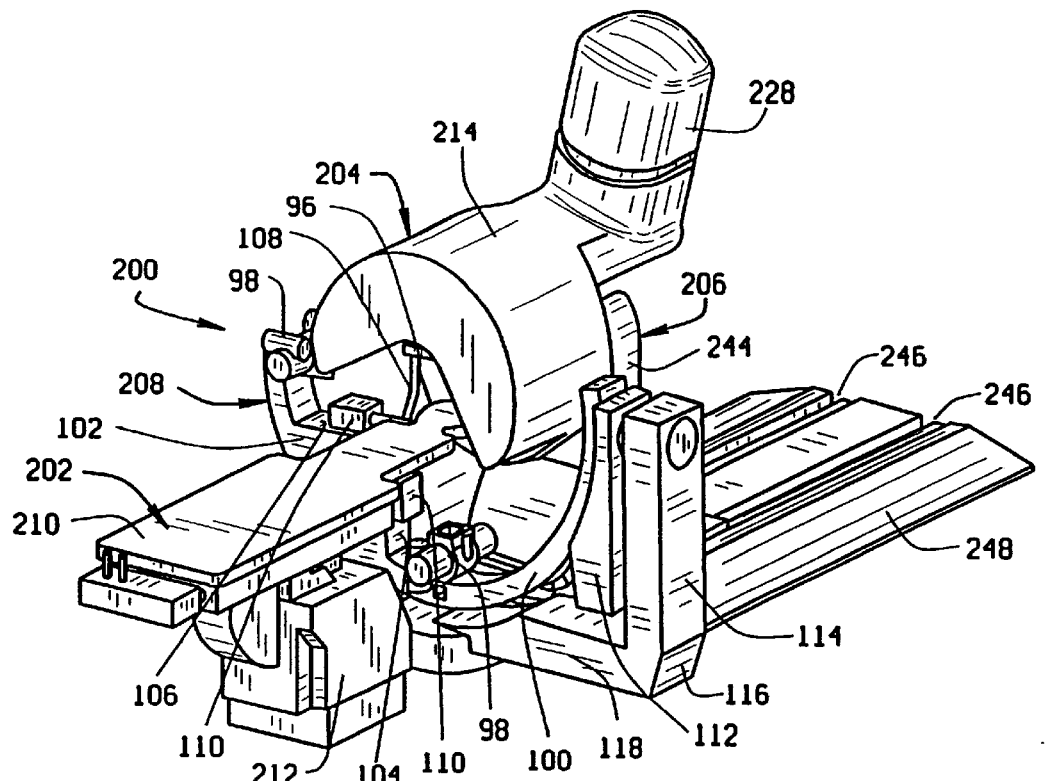
FIG. 23 is an isometric view of the magnetic navigation system of the second embodiment, showing the C-arm rotated 90° about the longitudinal horizontal axis.
Figure 24:
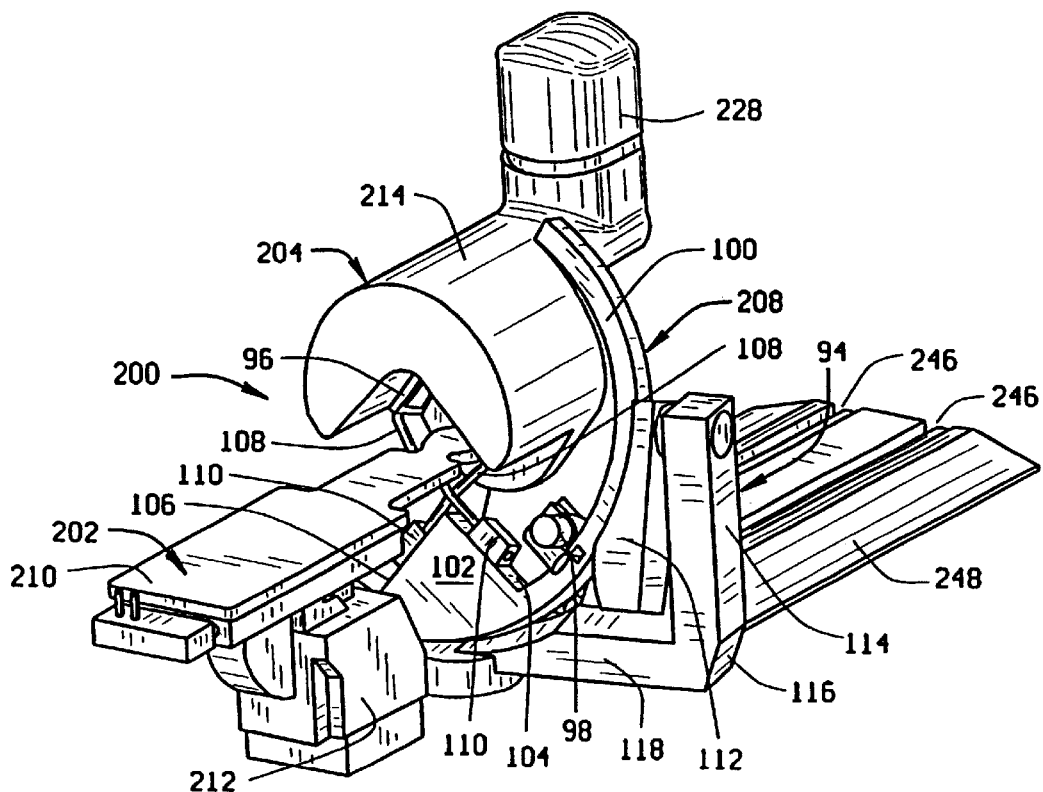
FIG. 24 is an isometric view of the magnetic navigation system of the second embodiment, showing the C-arm at a compound angle.
Figure 25:
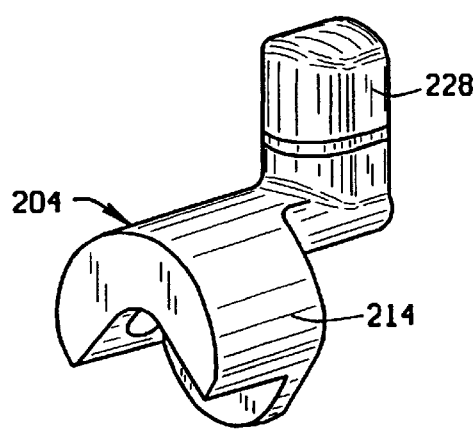
FIG. 25 is an isometric view of the magnet assembly of the second embodiment.
Figure 26:
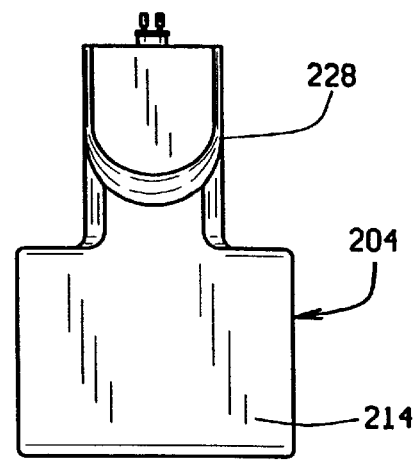
FIG. 26 is a top plan view of the magnet assembly of the second embodiment.
Figure 27:
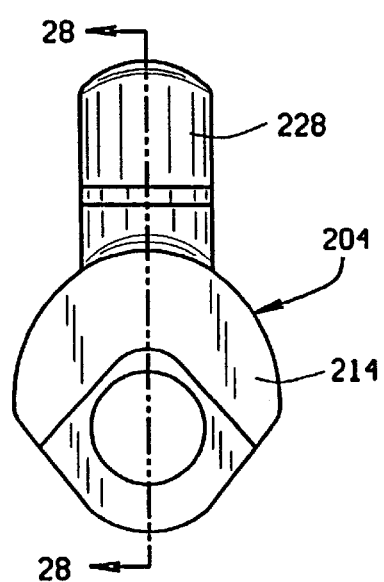
FIG. 27 is a front elevation view of the magnet assembly of the second embodiment.
Figure 28:
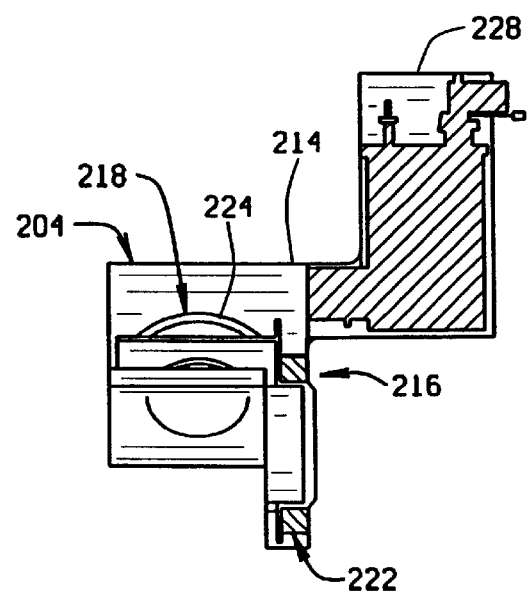
FIG. 28 is a vertical cross-sectional view of the magnet assembly of the second embodiment, taken along the plane of line 28—28 in FIG. 27.

The imaging assembly 208 is identical in construction to imaging assembly 58 (shown best in FIG. 2A), and corresponding parts are identified with corresponding reference numerals. The imaging devices 90 and 92 can be pivoted about a horizontal transverse axis as the body 112 tilts rearwardly (FIG. 21A) and forwardly (FIG. 21B) relative to the vertical leg 114 of the generally L-shaped bracket 116. The body 112 can pivot about 30° rearwardly and forwardly. The imaging devices 90 and 92 can be pivoted about a generally vertical axis as the horizontal leg 118 of generally L-shaped bracket 116 pivots rearwardly (FIG. 22A) and forwardly (FIG. 22B). The L-shaped bracket 116 can pivot about 30° rearwardly and forwardly. The imaging devices 90 and 92 can be rotated about a third axis as support 100 rotates relative to body 112 clockwise (FIG. 23) and counterclockwise (FIG. 19). The c-shaped support 100 can rotate 90° relative to body 112.

The imaging devices 90 and 92 provide bi-planar imaging of the portion of a patient's body inside the operating region of the magnet assembly 204. The support arms 108 are configured to clear the patient and the head of the bed, and support the imaging plates 96 in the space between the operating volume and magnet coils 222, 224 and 226 of the magnet assembly 204, while maintaining the imaging plates 96 aligned with their respective imaging beam sources 98. The imaging devices 90 and 92 can be moved around the operating region to accommodate movement of the magnet assembly 204 and to provide the most advantageous views of the operating region so that the surgeon can see the navigation of the medical device.

The Third Embodiment

Figure 34:
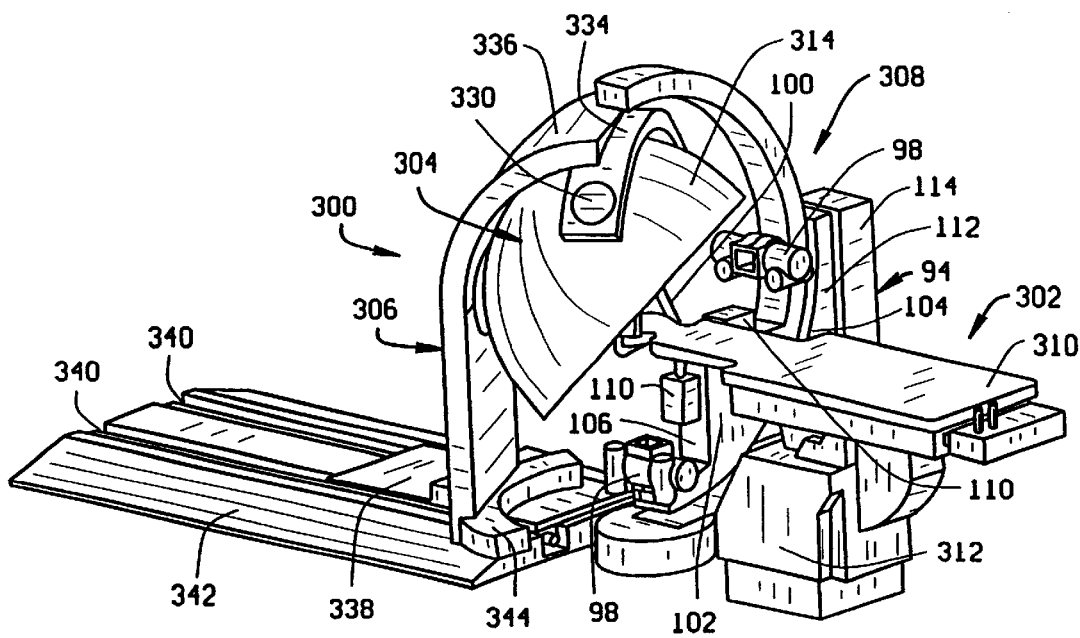
FIG. 34 is an isometric view of a third embodiment of a magnetic navigation system constructed according to the principles of this invention.
Figure 35:
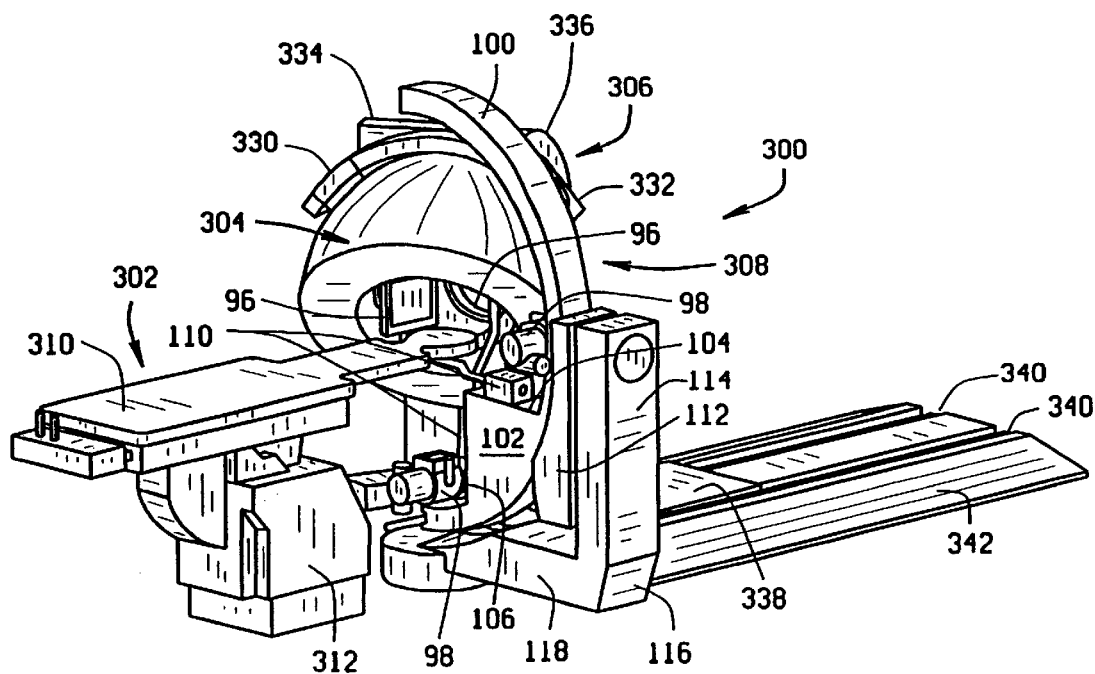
FIG. 35 is an isometric view of the magnetic navigation system of the third embodiment, with the magnet assembly rotated +30°.
Figure 36:
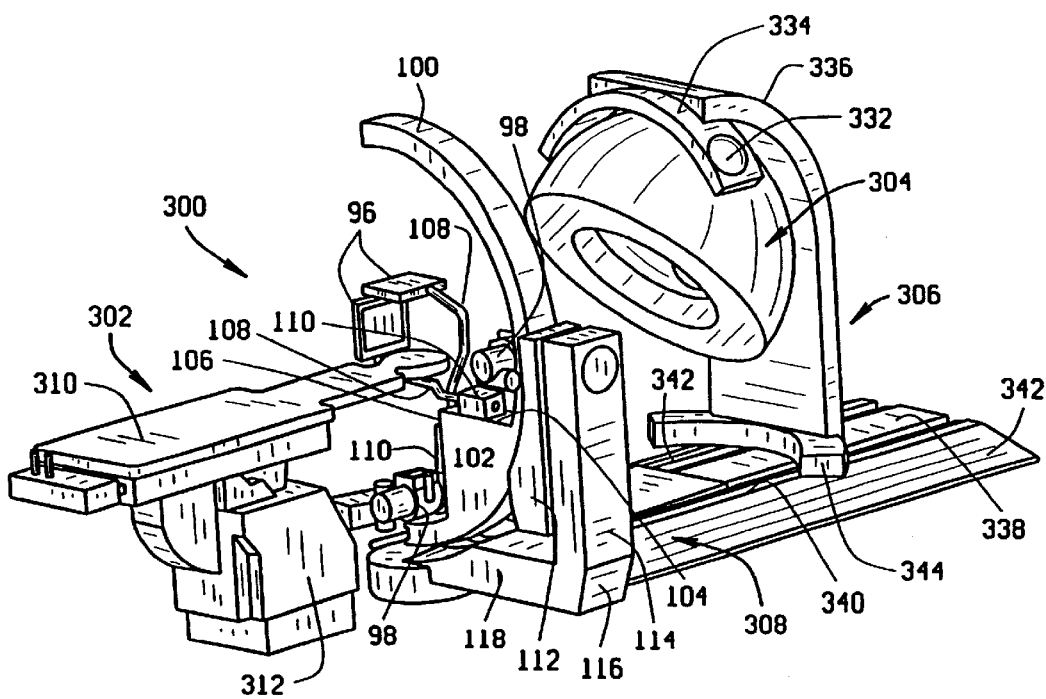
FIG. 36 is an isometric view of the magnetic navigation system of the third embodiment, with the magnet assembly retracted.
Figure 37:
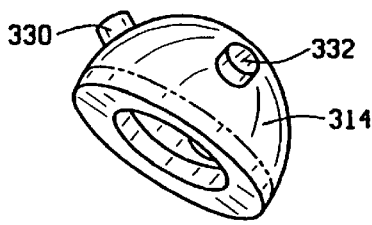
FIG. 37 is an isometric view of the magnet assembly of the third embodiment.
Figure 38:
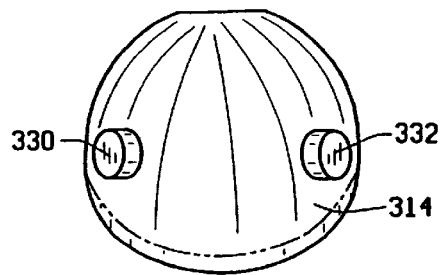
FIG. 38 is a top plan view of the magnet assembly of the third embodiment.
Figure 39:
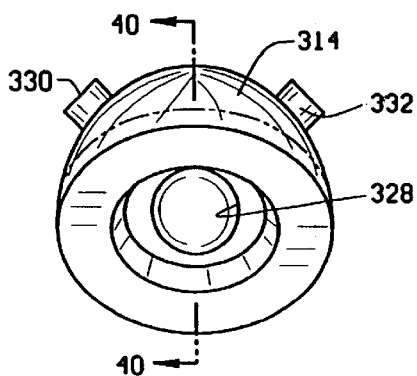
FIG. 39 is a front elevation view of the magnet assembly of the third embodiment.
Figure 40:
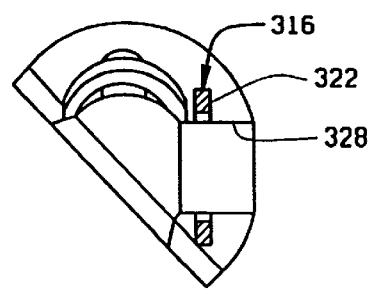
FIG. 40 is a vertical cross-sectional view of the magnet assembly of the third embodiment, taken along the plane of line 40—40 in FIG. 39.

A third embodiment of an inventive open field magnetic surgery system constructed according to the principles of this invention is indicated generally as 300 in FIGS. 34–36. The system 300 is similar in construction to systems 50 and 200, and comprises a patient support 302, a magnet assembly 304 on a moveable magnet support 306, and an imaging assembly 308.

The patient support 302 preferably comprises an elongate bed 310 mounted on a pedestal 312. The foot of the bed 310 is oriented toward the front of the system and the head of the bed is oriented toward the rear of the system. The head of the bed 310 is narrower than the foot of the bed so that it can fit inside the magnet assembly 304 and accommodate the imaging devices of the imaging assembly 308. The bed 310, is preferably moveable with respect to the pedestal 312 to allow the patient to be moved relative to the magnet assembly. The bed can be moved into and out of the system; raised and lowered, and rotated about its longitudinal axis. Other movements can be provided to facilitate positioning the patient relative to the operating volume of the magnet assembly.

The magnet assembly 304 comprises a generally hemispherical housing 314 containing three magnets 316, 318 and 320. The magnets 316, 318 and 320 are preferably magnet coils, and more preferably superconducting electromagnet coils 322, 324 and 326. The housing 314 contains suitable power and cooling apparatus to operate the superconducting coils.

The magnet coils 322, 324 and 326 are sized and arranged to provide a magnetic force within an operating region sufficient to move a magnetic medical device within that portion of a patient inside the operating region.

Figure 41:
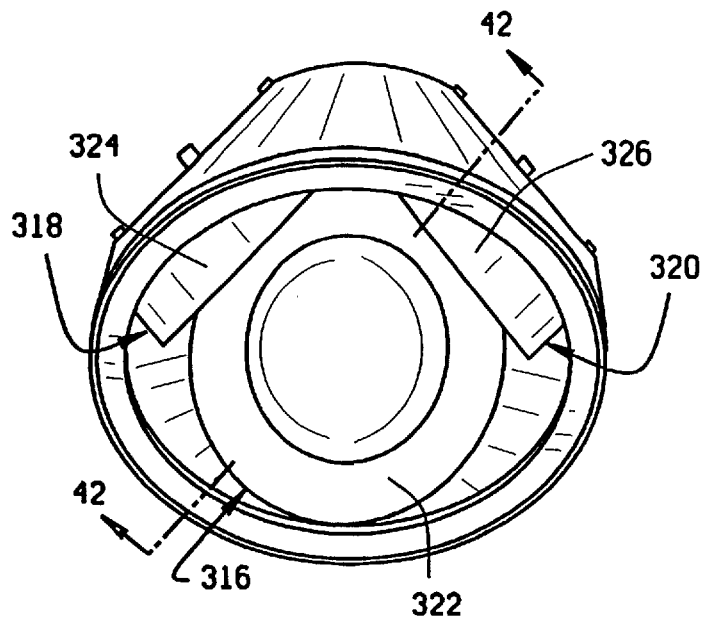
FIG. 41 is a front elevation view of the magnet assembly of the third embodiment, with the cover removed.
Figure 42:
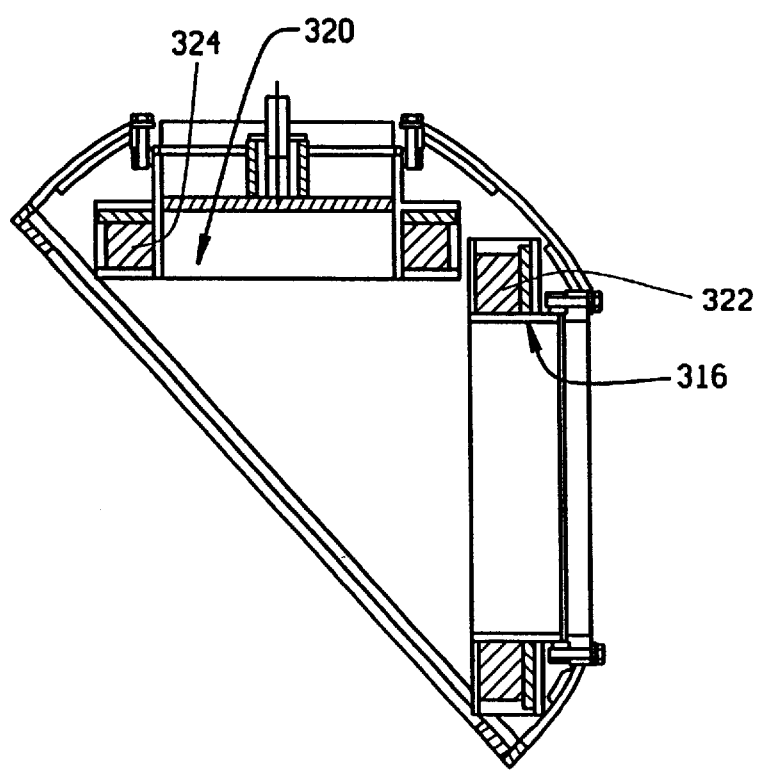
FIG. 42 is a cross-sectional view of the magnet assembly of the third embodiment, taken along the plane of line 42—42 in FIG. 41.
Figure 43:
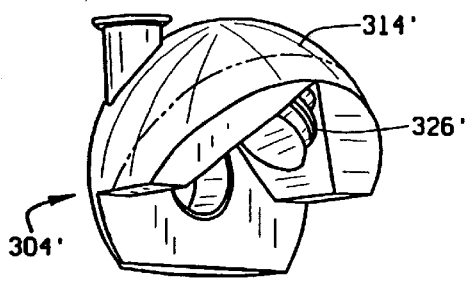
FIG. 43 is an isometric view of an alternate construction of the magnet assembly of the third embodiment, with a portion broken away to reveal the position of one of the magnets.
Figure 44:
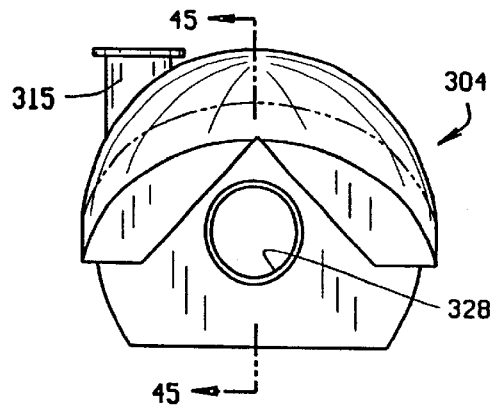
FIG. 44 is a front elevation view of the alternate construction of the magnet assembly of the third embodiment.
Figure 45:
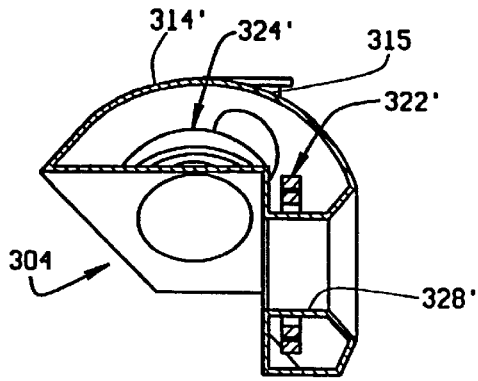
FIG. 45 is a vertical cross-sectional view of the magnet assembly of the third embodiment, taken along the plane of line 45—45 in FIG. 44.
Figure 46:
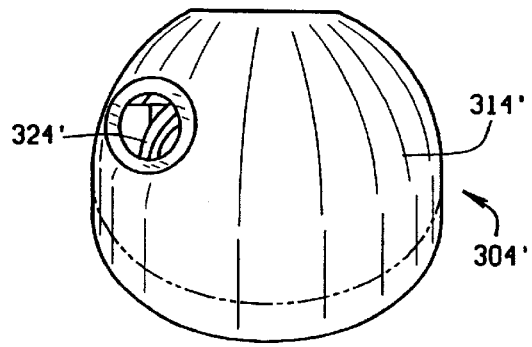
FIG. 46 is a vertical cross-sectional view of the magnet assembly of the third embodiment.
Figure 47:
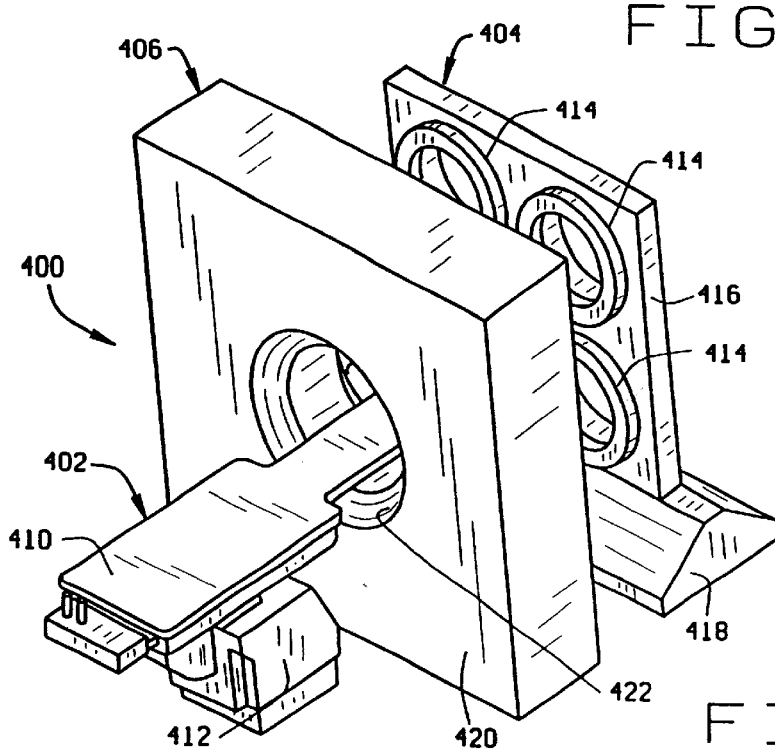
FIG. 47 is an isometric view of a fourth embodiment of a magnetic navigation system in accordance with the present invention.
Figure 48:
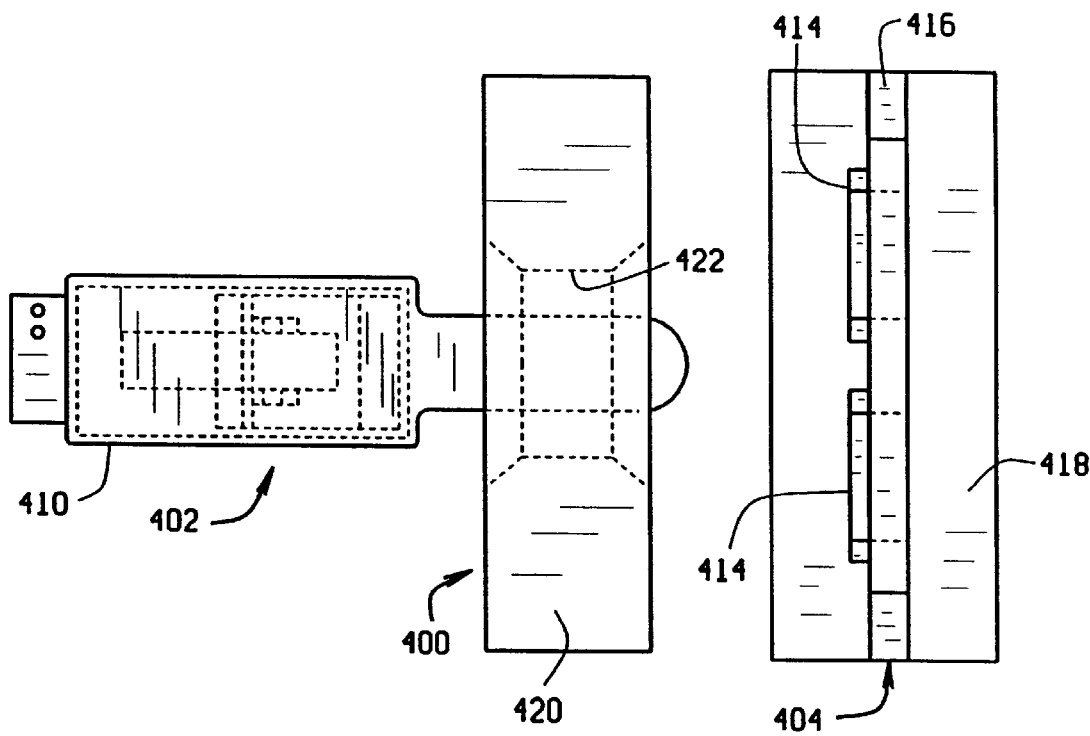
FIG. 48 is a top plan view of the magnetic navigation system of the fourth embodiment.
Figure 49:
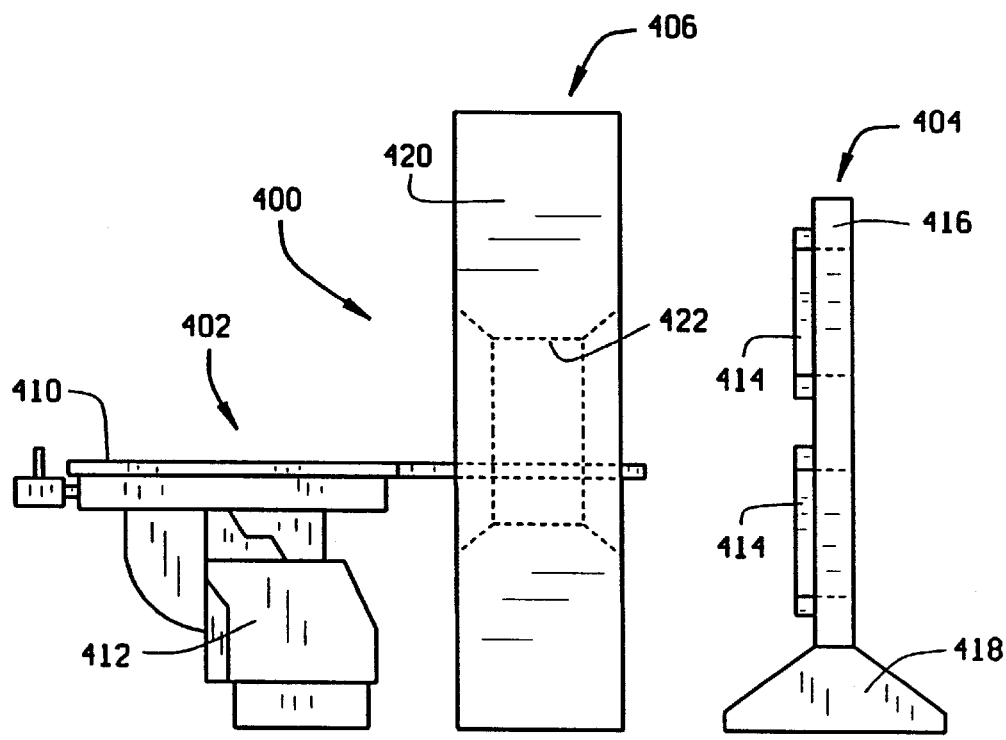
FIG. 49 is a right side elevation view of the magnetic navigation system of the fourth embodiment.
Figure 50:
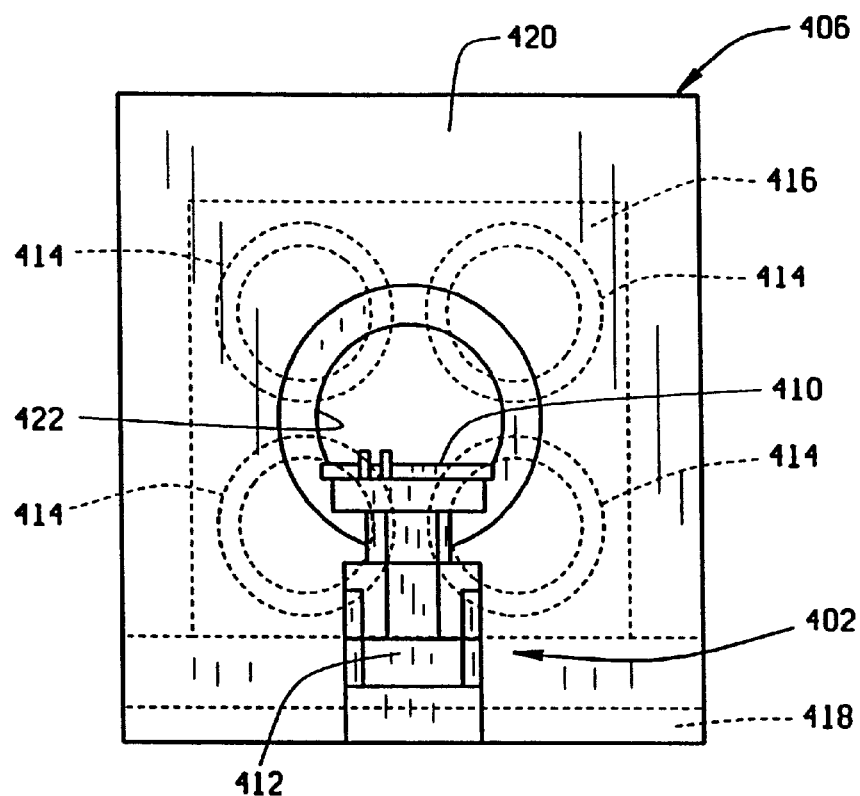
FIG. 50 is a front elevation view of the magnetic navigation system of the fourth embodiment.
Figure 51:
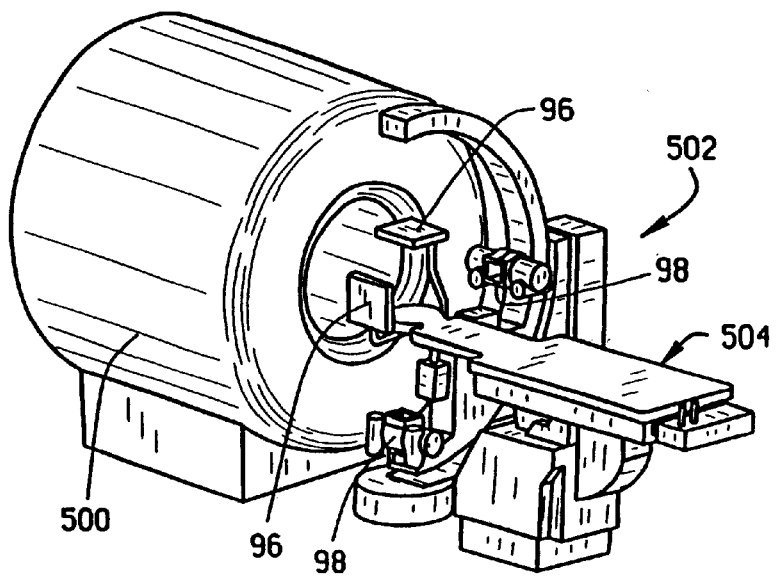
FIG. 51 is an isometric view of a combination of a magnetic resonance imaging device and a bi-planar imaging device.
Figure 52:
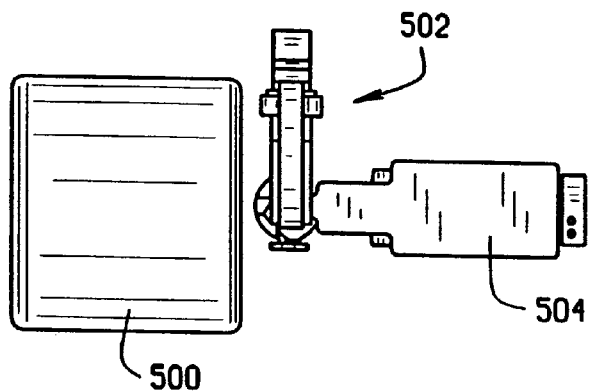
FIG. 52 is a top plan view of the combination magnetic resonance imaging device and bi-planar imaging device.
Figure 53:
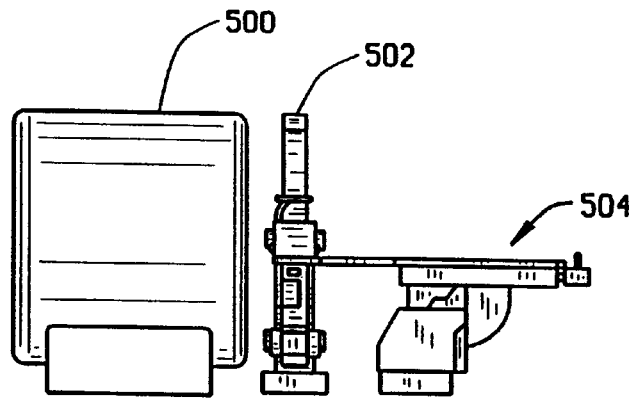
FIG. 53 is a side elevation view of the combination magnetic resonance imaging device and bi-planar imaging device.
Figure 54:
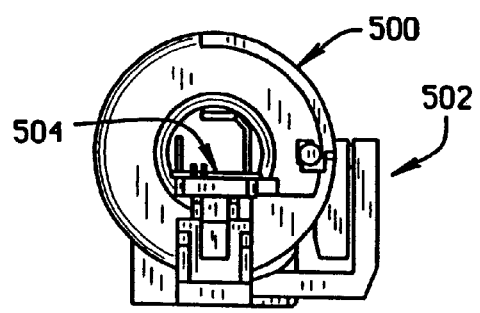
FIG. 54 is an end elevation view of the combination magnetic resonance imaging device and bi-planar imaging device.

As best shown in FIGS. 41 and 42 the coils 322, 324 and 326 are preferably arranged in three mutually perpendicular planes such that the axes of the three coils intersect generally in the center of the operating region. Coil 322 is arranged so that it is normally in a vertical transverse plane, with its axis extending generally longitudinally, parallel to the longitudinal axis of the patient support 302. In this third preferred embodiment, the coil 322 has 26.09 inch outer diameter, a 19.01 inch inner diameter, and a thickness of 2.62 inches.

Coils 324 and 326 are similar in construction and are preferably oriented in mutually perpendicular planes that are perpendicular to the plane of coil 322. Each of the coils 324 and 326 has an outside diameter of 21.83 inches, an inside diameter of 15.75 inches, and a thickness of 2.85 inches. The faces of the coils 324 and 326 are spaced 11.90 inches from the axis of coil 322, and the face of coil 322 is spaced 12.75 inches from the axes of the coils 324 and 326.

The housing 314 preferably has an opening 328 therein aligned with the central opening of coil 322 so that a portion of the patient support and/or the patient can extend therethrough, to bring the desired portion of the patient within the operating volume.

An alternate construction of the magnet assembly of this third embodiment is indicated generally as 304' in FIGS. 43–46. The magnet assembly 304' comprises a generally hemispherical housing 314'. The housing has a cold head mounting assembly 315 for connecting the magnet assembly 304 to a cooling system. Inside the housing 314' the three magnets 322', 324', and 326'. The coils 322', 324' and 326' are preferably arranged in three mutually perpendicular planes such that the axes of the three coils intersect generally in the center of the operating region. Coil 322' is arranged so that it is normally in a vertical transverse plane, with its axis extending generally longitudinally, parallel to the longitudinal axis of the patient support 302. In this third preferred embodiment, the coil 322' has 24.22 inch outer diameter, a 17.4 inch inner diameter, and a thickness of 2.62 inches.

Coils 324' and 326' are similar in construction and are preferably oriented in mutually perpendicular planes that are perpendicular to the plane of coil 322'. Each of the coils 324' and 326' has an outside diameter of 22.56 inches, an inside diameter of 16.14 inches, and a thickness of 3.05 inches. The faces of the coils 324' and 326 are spaced 11.94 inches from the axis of coil 322', and the face of coil 322' is spaced 12.81 inches from the axes of the coils 324' and 326'.

The housing 314' preferably has an opening 328' therein aligned with the central opening of coil 322' so that a portion of the patient support and/or the patient can extend therethrough, to bring the desired portion of the patient within the operating volume.

The housing 314 has trunions 330 and 332 projecting from its exterior. These trunions 330 and 332 are connected to a band 334, that is mounted on an inverted "J" shaped support 336. The band 334 and the support 336 suspend the housing 314 so that the axis of the generally hemispherical housing 314 extends at an angle with respect to vertical and horizontal, so that the housing faces generally downwardly. The axis preferably forms an angle of about 45° with respect to horizontal. The support 336 is mounted to a platform 338 which is slidably mounted in tracks 340 in base 342. Thus the support 336 (and the housing 314) can be moved forward (toward the patient support as shown in FIG. 35) and rearward (away from the patient support as shown in FIG. 36). The support 336 has a circular bottom 344 which can slide relative to the platform 338 so that the housing 314 pivots, preferably about a vertical axis that extends through the point of an intersection of the axes of the three magnet coils 322, 324 and 326. In this third preferred embodiment, the housing 314 can pivot 30° toward each side.

The imaging assembly 308 is identical to the imaging assembly 208 of the second embodiment and the imaging assembly 58 of the first embodiment, and corresponding parts are identified with corresponding reference numerals.

The imaging devices 90 and 92 can be pivoted about a horizontal transverse axis as the body 112 tilts rearwardly and forwardly relative to the vertical leg 114 of the generally L-shaped bracket 116. The body 112 can pivot about 30° rearwardly and forwardly. The imaging devices 90 and 92 can be pivoted about a generally vertical axis as the horizontal leg 118 of generally L-shaped bracket 116 pivots rearwardly and forwardly. The L-shaped bracket 116 can pivot about 30° rearwardly and forwardly. The imaging devices 90 and 92 can be rotated about a third axis as support 100 rotates relative to body 112 clockwise and counterclockwise. The C-shaped support 100 can rotate 90° relative to body 112.

The Fourth Embodiment

A fourth embodiment of an inventive open field magnetic surgery system constructed according to the principles of this invention is indicated generally as 400 in FIGS. 47–50. The system 400 comprises a patient support 402, a magnet assembly 404, and a CT imaging assembly 406.

The patient support 402 preferably comprises an elongate bed 410 mounted on a pedestal 412. The foot of the bed 410 is oriented toward the front of the system and the head of the bed is oriented toward the rear of the system. The head of the bed 410 is narrower than the foot of the bed so that it can fit inside the magnet assembly 404 and accommodate the imaging devices of the imaging assembly 406. The bed 410, is preferably moveable with respect to the pedestal 412 to allow the patient to be moved relative to the magnet assembly. The bed can be moved into and out of the system; raised and lowered, and rotated about its longitudinal axis. Other movements can be provided to facilitate positioning the patient relative to the operating volume of the magnet assembly.

The magnet assembly 404 comprises a plurality (in this fourth preferred embodiment four) magnet coils 414 arranged on planar support 416, on a base 418. The magnet coils 414 are capable of generating a magnetic field in an operating region of sufficient strength to navigate a magnetic medical in the portion of the patient within the operating region. The coils may all have parallel axes, but this is not essential and some or all of the coils may be oriented out of the plane of planar support 416.

The imaging assembly 406 comprises a compact CT imaging device 420 adapted to provide real time or near real time CT images of the operating region. The CT imaging device 420 has an opening 422 through which a portion of the patient support 402 and/or the patient can extend to allow the surgeon to bring virtually any portion of the patient's body within the operating region of magnet assembly 404. The CT imaging device is one that is not significantly affected by the proximity of the magnets 414.

It should be noted that the same or a very similar magnetic and imaging equipment and arrangement may be used to provide for parenchymal navigation for neurosurgical procedures in brain tissue, such as for implanting catheters or introducing tubes in curved paths. See Werp et al., "Method of and apparatus for intraparenchymal positioning of medical devices," app. Ser. No. 08/969,165, filed Nov. 12, 1997; "Apparatus for and Method of Controlling an Electromagnetic Coil System," app. Ser. No. 08/682,867, filed Jul. 8, 1996; Ritter et al., "Control Method for Magnetic Stereotaxis System," U.S. Pat. No. 5,654,864, issued Aug. 5, 1997; Howard et al., "Magnetic Stereotactic System for Treatment Delivery," U.S. Pat. No. 5,125,888, issued Jun. 30, 1992; Howard et al., "Magnetic Stereotactic System for Treatment Delivery," U.S. Pat. No. 5,707,335, issued Jan. 13, 1998; Howard et al., "Video Tumor Fighting System," U.S. Pat. No. 4,869,247, issued Sep. 26, 1989; Howard et al., "Magnetic Stereotactic System for Treatment Delivery," U.S. Pat. No. 5,779,694, issued Jul. 14, 1998; Howard et al., "Magnetic Stereotactic System for Treatment Delivery," app. Ser. No. 09/114,414, filed Jul. 13, 1998; "Method and Apparatus for Magnetically Controlling Motion Direction of a Mechanically Pushed Catheter," app. Ser. No. 08, 920,446, filed Aug. 29, 1997; and Ritter et al., "Method and Apparatus for Rapidly Changing a Magnetic Field Produced by Electromagnets," app. Ser. No. 08/921,298, filed Aug. 29, 1997. Further applications of the inventive apparatus include the introduction of biopsy tools, electrodes for palidotomy, or stimulators for other treatment of Parkinson's disease, and the introduction of drug infusion apparatus.

A combination of a magnetic resonance imaging device and a bi-planar imaging device is shown in FIGS. 51–54. The combination includes a conventional magnetic resonance imaging device 500 and a bi-planar imaging assembly 502, which is preferably identical to imaging assembly 58, shown best in FIG. 2A. This allows the patient to be imaged with the MRI and then imaged with the bi-planar imaging assembly close in time, without having to transport the patient from place to place to obtain the images. This facilitates calibration of the MRI and the bi-planar x-ray images used during magnetic surgery. The combination includes a patient support 504, which is similar in construction to patient support 52, described above. This allows the patient to be moved into and out of the MRI 500 and into and out of the bi-planar imaging assembly 502. The close proximity of the MRI 500 and the bi-planar imaging assembly 502 is permitted in part by the use of amorphous silicon imaging plates, or some other imaging receptor, that is minimally affected by the significant magnetic fields adjacent the MRI 500.

It will be recognized by one skilled in the art that the various embodiments shown and described herein are intended to be exemplary, that many modifications may be made within the spirit and scope of the invention. It should also be clear that embodiments are possible that incorporate some, but not all, of the features of the invention, such as, by way of example only, providing fewer directions of motion for a C-arm. Such embodiments may still fall within the scope and spirit of the invention, even though achieving only some of the objectives and advantages thereof. The scope of the invention should therefore be determined from the claims, including all legal equivalents thereto, with reference to the specification and the examples and figures provided therein.

What is claimed is:

1. A system for navigating a magnetic medical device within that part of a patient located within an operating region of the system, the system comprising:

at least three magnets configured and arranged in a hemispherically shaped shell to provide a magnetic field effective within the operating region to navigate the magnetic medical device within the operating region.

2. A system for navigating a magnetic medical device within that part of a patient located within an operating region of the system, the system comprising:

at least three magnet coils configured and arranged in an open concave shell to provide a magnetic field effective within the operating region to navigate the magnetic medical device within the operating region.

3. The system according to claim 2 wherein the shell has an opening through which a portion of the patient can extend into the operating region without passing though one of the coils.

4. A system for navigating a magnetic medical device within that part of a patient located within an operating region of the system, the system comprising:

a single magnet arranged and configured to provide a magnetic field along at least one of a plurality of oblique axes extending through the operating region, one or more magnets arranged and configured to provide a magnetic field along each of the other of said oblique axes, said magnetic fields being effective to controllably navigate the medical device within substantially the entirety of the operating region.

5. A system for navigating a magnetic medical device within that part of a patient located within an operating region of the system, the system comprising:

a plurality of magnet coils mounted within one or more supports, said magnet coils being effective to controllably navigate the medical device within substantially the entirety of the operating region, said operating region being positioned so that said part of the patient may be located within the operating region without passing through any of said magnet coils.

6. A system for navigating a magnetic medical device within that part of a patient located within an operating region of the system, the system comprising:

a plurality of magnets effective for creating a magnetic field sufficient to navigate said medical device within said operating region, said plurality of magnets being generally aligned along a plurality of oblique axes with only a single one of said magnets being aligned along one of said axes, and one or more magnets being aligned along the others of said axes.

7. The system according to claim 6 wherein the axes extend through the operating region of the system.

8. A system for navigating a magnetic medical device within that part of a patient located within an operating region of the system, the system comprising:

a plurality of magnets mounted within one or more supports, said magnets being effective to controllably navigate the medical device within substantially the entirety of the operating region, a patient support for supporting a patient intended to be located within said operating region, said patient support being moveable with respect to said supports for said magnets, said patient support being positioned with respect to said magnets so that as said patient support is advanced toward said magnets, said patient is moved into said operating region before said patient passes through the bore of any magnet.

9. A system for navigating a magnetic medical device within that part of a patient located within an operating region, the system comprising:

a plurality of navigating magnets effective to controllably navigate the medical device with substantially the entirety of the operating region, and a patient support for moving the patient into the operating region of the system, only a single one of said magnets having its central axis generally aligned with the direction of movement of the patient support, and the others of said magnets being aligned with a plurality of oblique axes extending through the operating region.

10. A system for navigating a magnetic medical device within that part of a patient located within an operating region of the system, the system comprising:

a total of three navigating magnets configured and arranged to provide a magnetic field effective within the operating region to navigate the magnetic medical device within the operating region.

11. The system according to claim 10 wherein the magnets are capable of providing a magnetic field of at least about 0.1 Tesla anywhere in an operating region of at least about two inches by about two inches by about two inches.

12. The system according to claim 11 wherein the magnets are capable of providing a magnetic field of at least about 0.1 Tesla anywhere in an operating region of at least about five inches by about five inches by about five inches.

13. The system according to claim 10 wherein the magnets are capable of providing a magnetic field of at least about 0.3 Tesla anywhere in an operating region of at least about two inches by about two inches by about two inches.

14. The system according to claim 13 wherein the magnets are capable of providing a magnetic field of at least about 0.3 Tesla anywhere in an operating region of at least about five inches by about five inches by about five inches.

15. The system according to claim 10 wherein the center of the operating region is spaced at least about twelve inches from each magnet.

16. The system according to claim 10 wherein the magnets are electromagnetic coils.

17. The system according to claim 16 wherein the electromagnet coils are superconducting electromagnetic coils.

18. The system according to claim 16 wherein the operating region has a volume of at least about five inches by about five inches by about five inches.

19. The system according to claim 16 wherein the coils are sized and arranged so that the axes of any two coils lie in the same plane.

20. The system according to claim 16 wherein the coils are mutually perpendicular.

21. The system according to claim 16 wherein the axes of the coils intersect.

22. The system according to claim 16 wherein the axes of the coils intersect in the operating region.

23. The system according to claim 16 wherein the intersection of the axes of the magnets is at least about six inches from each of the coils, but no more than about fifteen inches from each of the coils.

24. The system according to claim 16 wherein the center of the operating region is at least six inches from each of the coils, but no more than about fifteen inches from each of the coils.

25. The system according to claim 16 wherein the coils are arranged and configured so that their axes intersect, and wherein the coils are spaced sufficiently from the point of intersection to accommodate a sphere centered on the point of intersection, with a radius of at least twelve inches.

26. The system according to claim 16 wherein the coils are arranged in a generally hemispherically shaped shell.

27. The system according to claim 26 wherein the generally hemispherically shaped shell is mounted so that the axis is at an angle with respect to vertical.

28. The system according to claim 27 wherein the generally hemispherically shaped shell is mounted for rotation about a vertical axis.

29. The system according to claim 26 wherein there is an opening in the shell, aligned with the center of one of the coils through which a portion of the patient's body can extend.

30. The system according to claim 26 wherein the generally hemispherically shaped shell has an inner diameter greater than about twenty-five inches and an outer diameter less than about fifty inches.

31. The system according to claim 16 further comprising an imaging system comprising at least one imaging plate and an x-ray imaging source, the imaging system being movably mounted independently of the coils so that the imaging plate can be moved to positions between the patient and the coils.

32. The system according to claim 31 wherein the imaging system comprises at least two imaging plates and two x-ray imaging sources, and wherein each imaging plate and its respective x-ray source is movably mounted independently of the coils so that the imaging plates can be moved to positions between the patent and the coils.

33. The system according to claim 32 wherein each imaging plate and its respective x-ray source is fixedly mounted with respect to the other.

34. The system according to claim 32 wherein the lines between each imaging plate and its respective x-ray source are perpendicular.

35. The system according to claim 10 wherein said system comprises only three magnets and each of said magnets further comprises a superconducting magnet coil, said coils being generally arranged along the axes of an orthogonal coordinate system.

36. The system according to claim 35 wherein the origin of said orthogonal coordinate system is controlled to be within the operating region.

37. The system according to claim 36 wherein said coils are mounted to a generally hemispherically shaped shall, and wherein each coil has its central axis aligned along an axis of said orthogonal coordinate system.

38. The system according to claim 37 further comprising a support for the patient, and a moveable support for the shell so that said shell may be reoriented about said patient support and patient.

39. The system according to claim 38 wherein one of said coils has its central axis generally aligned with a central axis of the patient.

40. The system according to claim 39 wherein said operating region comprises a sphere shaped space having a radius of approximately two and one half inches and centered at approximately the coordinate system origin.

41. The system according to claim 40 wherein the shell and the coils are positioned to lie outside the operating region.

42. The system according to claim 41 further comprising a transport mechanism connecting the moveable shell support to the patent support for moving the shell about the patient support.

43. The system according to claim 42 wherein said coils are positioned so that their respective near field lines are substantially straight within the operating region.

44. The system according to claim 43 wherein each of said coils are sized to provide a field strength of at least about 0.3 Tesla.

45. The imaging system of claim 10 wherein the electromagnetic coils are configured to provide a magnetic field adjustable up to at least about 0.3 Tesla anywhere in the operating region.

46. A system for navigating a magnetic medical device within a patient, the system comprising a medical imaging device configured to provide an image of an operating region of a patient including the medical device therein; and
 a total of three navigating magnets configured and arranged to provide a magnetic field effective within the operating region to orient the magnetic medical device with in the operating region.

47. The system according to claim 46 wherein the magnets are electromagnetic coils.

48. The system according to claim 47 wherein the electromagnet coils are superconducting electromagnetic coils.

49. The system according to claim 47 wherein the imaging device comprises at least one imaging plate and associated x-ray source, and a support for mounting imaging plate and x-ray source for movement independent of the coils, the support permitting the imaging plate to be moved to positions between the patient and the coils.

50. The system according to claim 49 wherein the imaging device comprises at least two imaging plates and associated x-ray sources, and a support for mounting the imaging plates and x-ray sources for movement independent of the coils, the support permitting the imaging plates to be moved to positions between the patient and the coils.

51. The system according to claim 50 wherein the support is movable about three generally perpendicular axes.

52. The system according to claim 51 wherein the axes of the three coils intersect and wherein the three generally perpendicular axes of movement of the support each extend through the point of intersection.

53. The system according to claim 51 wherein lines between each imaging plate and its respective x-ray source are perpendicular.

54. The system according to claim 53 wherein each imaging plate and its x-ray source are fixedly mounted on the support with respect to the other.

55. The system according to claim 52 wherein the axes of the three coils intersect; wherein the three coils are mounted in a frame for movement about at least one axis extending through the point of intersection; and wherein the imaging device comprises at least one imaging plate and an x-ray source on a support, the support being movable about at least one axis that extends through the point of intersection.

56. A system for navigating a magnetic medical device within an operating region within a patient, the system comprising:

three electromagnetic coils configured and arranged to be able to provide a magnetic field of at least about 0.1 Tesla within an operating region at least about five inches by about five inches by about five inches which operating region is spaced at least about twelve inches from each of the coils, to selectively orient the magnetic medical device anywhere within the operating region.

57. The system according to claim 56 wherein the three electromagnetic coils are capable of providing a magnetic field of at least about 0.3 Tesla anywhere within the operating region.

58. The system according to claim 56 wherein the axes of three electromagnetic coils are mutually perpendicular.

59. The system according to claim 58 wherein the axes of the three electromagnetic coils intersect.

60. The system according to claim 59 wherein the three coils are mounted in a shell having a generally hemispherical shape.

61. The system according to claim 60 wherein the hemispherical shell is oriented so that its axis is at an angle greater than 0° and less than 90° with respect to vertical.

62. The system according to claim 61 wherein the shell is rotatably mounted about a vertical axis.

63. The system according to claim 62 wherein the coils are arranged so that their axes intersect at a point, and wherein the vertical axis of rotation of the shell extends through the point of intersection of the axes.

64. The system according to claim 56, further comprising a medical imaging device including at least one amorphous silicon plate imaging detector.

65. The system according to claim 56 wherein the three electromagnetic coils are fixed relative to one another and moveable relative to the patient.

66. The system according to claim 56 further comprising a medical imaging device, wherein the medical imaging device comprises at least one imaging plate that can be interposed between one of the three electromagnetic coils and the operating region.

67. The system according to claim 66 wherein the medical imaging device comprises first and second x-ray sources and corresponding first and second image plates for providing images of the operating region in two planes.

68. The system according to claim 56 further comprising a medical imaging device for providing images of the operating region in two perpendicular planes.

69. The system according to claim 68 wherein the coils are mounted in a generally hemispherically shaped shell, and wherein the image plates can extend into the shell in position between the operating region and at least one of the electromagnetic coils.

70. The system according to claim 69 wherein the medical imaging device is movable relative to the operating zone, independently of the magnet coils.

71. A system for navigating a magnetic medical device within an operating region within which a patient may be placed, the system comprising:

a total of three super conducting magnets configured such that each of their central axes lies generally along an axis of an orthogonal coordinate system having its origin approximately centered within said operating region, said magnets being supported by a generally hemispherical shell and each magnet being of sufficient strength to provide a magnetic field in the direction of its respective central axis having a generally consistent strength of about 0.3 Tesla throughout substantially the entirety of said operating region, and a control for adjusting the strength of the magnetic field of each of said magnets to thereby controllably navigate the magnetic medical device within the patient as the patient lies with a part of the patient's body within the operating region.

72. A system for navigating a magnetic medical device within an operating region within a patient, the system comprising:

a support for at least a portion of the patient;

a magnet hood including three electromagnetic coils arranged and configured so that the axes of the coils converge, a magnet mount holding the magnet hood so that the convergence of the axes would be within the operating region of the patient supported on the support;

an x-ray imaging assembly for providing an image of the operating region of a patient supported on the patient support, the imaging assembly comprising at least one imaging plate and an x-ray imaging beam source mounted on an imaging support to be on opposite sides of the operating region, and a C-arm mechanism for selectively pivoting the support about three mutually perpendicular axes.

73. The system according to claim 72 wherein the C-arm mechanism pivots the imaging support about three mutually perpendicular axes that extend through the operating region.

74. The system according to claim 72 wherein the C-arm mechanism pivots the imaging support about three mutually perpendicular axes that extend through point where the axes of the three magnets converge.

75. The system according to claim 74 wherein axes of the magnets intersect, and wherein the magnet mount mounts the magnet hood to pivot about at least one axis that extends through the point where the axes of the three magnets intersect.

76. A system for navigating a magnetic medical device through the part of a patient within an operating region of the system while providing an open environment around the patient, the system comprising:

a support for the patient;

a magnet hood assembly including a magnet hood supported by a magnet hood mount, the magnet hood having three navigating electromagnets configured to provide a selected magnetic field in the operating region; and an x-ray imaging assembly including a portion disposed between the magnet hood and the operating region to provide a medical image of the operating region.

77. The system of claim 76 wherein the three electromagnets are electromagnetic coils configured to have essentially mutually perpendicular axes that converge in the operating region.

78. The system of claim 76 wherein the imaging assembly comprises:

a imaging support;

a mechanism for moving the imaging support relative to the patient;

an imaging plate operatively supported by the imaging support;

an imaging tube producing an imaging beam directed towards the imaging plate through the operating region, the imaging tube also being operatively supported by the imaging support so that movement of the imaging tube and the imaging plate are coordinated upon movement of the support, the imaging beam remaining directed toward the imaging plate through the operating region in at least a plurality of different positions of the support; and at least one of the imaging tube and the imaging plate is disposed between the magnet assembly and the operating region in said plurality of different positions of the support.

79. The system of claim 78 wherein the magnet hood is moveably attached to the magnet hood support base in a manner to allow repositioning about the operating region separately from movement of the imaging assembly to provide greater freedom in imaging the operating region of the patient.

80. The system of claim 78 wherein at least one of the imaging tube and the imaging plate is adjustably supported by the support so that a distance between the imaging tube and the imaging plate is adjustable.

81. The system of claim 78 wherein the imaging plates are amorphous silicon imaging plates to provide immunity of the imaging system to strong magnetic fields.

82. The system of claim 78 wherein the magnet hood is moveably attached to the magnet hood support base in a manner to allow repositioning about the operating region.

83. The system of claim 78 wherein the electromagnetic coils are configured to provide a magnetic field adjustable up to at least 0.3 Tesla in the operating region without flexure of the magnet hood in excess of 1 millimeter from the adjustable magnetic field, and in which the electromagnetic coils are superconducting and include an associated cryogenic system on or supported by the magnetic hood, or both, and wherein the magnet hood, including the associated cryogenic system and electromagnetic coils, weigh less than about 5000 pounds.

84. The system of claim 78 wherein the three electromagnetic coils are confined within a magnet support hood having a generally hemispherical shape.

85. The system of claim 84 wherein the medical imaging device comprises movable imaging plates and movable imaging tubes having imaging beams directed towards the imaging plates through an operating region of a patient, and the magnet support hood has an axis of symmetry tilted to increase access of the imaging beams to the operating region of the patient.

86. The system of claim 85 wherein the magnet hood is rotatable about an axis.

87. A method of navigating a magnetic medical device within an operating region in a patient, the method comprising:

applying a magnetic field to the magnetic medical device in the operating zone with at least three electromagnetic coils contained within a magnet shell to navigate the medical device within the operating region; and providing an image of the magnetic medical device in the operating region with an imaging apparatus comprising at least one imaging plate and an x-ray imaging beam source, the imaging plate and the x-ray imaging beam source being on opposite sides of the operating region, with the imaging plate being positioned between the operating region and the magnet shell.

88. A method of navigating a magnetic medical device within an operating region in a patient, the method comprising:

applying a magnetic field to the magnetic medical device in the operating region with at least three electromagnetic coils contained within a magnet shell having a concave opening to navigate the medical device within the operating region, the axes of the coils intersecting at a point in the operating region, while providing a real-time image of the magnetic medical device in the operating region with an imaging apparatus comprising at least one imaging plate and an imaging beam source, the imaging plate and imaging beam source being on opposite sides of the operating region, with the imaging plate being positioned between the operating region and the magnet shell.

89. The method according to claim 88 wherein the imaging plate and imaging beam source are movable about three mutually perpendicular axes which extend through the operating zone.

90. The method according to claim 89 wherein the imaging plate and imaging beam source are movable about three mutually perpendicular axes which extend through the point of intersection of the axes of the magnet.

* * * * *